(12) United States Patent
Metcalf et al.

(10) Patent No.: US 12,076,215 B2
(45) Date of Patent: Sep. 3, 2024

(54) METHODS AND DEVICES TO DISRUPT AND CONTAIN PATHOGENS

(71) Applicant: CONVATEC LIMITED, Deeside (GB)

(72) Inventors: Daniel Metcalf, Deeside (GB); Manjunath Penagondla, Deeside (GB)

(73) Assignee: CONVATEC LIMITED, Deeside (GB)

( * ) Notice: Subject to any disclaimer, the term of this patent is extended or adjusted under 35 U.S.C. 154(b) by 333 days.

(21) Appl. No.: 16/891,632

(22) Filed: Jun. 3, 2020

(65) Prior Publication Data

US 2020/0375802 A1 Dec. 3, 2020

Related U.S. Application Data

(60) Provisional application No. 62/856,676, filed on Jun. 3, 2019.

(51) Int. Cl.
*A61F 13/0203* (2024.01)
*A61F 13/00* (2024.01)
(Continued)

(52) U.S. Cl.
CPC .... *A61F 13/0213* (2013.01); *A61F 13/00063* (2013.01); *A61F 13/0206* (2013.01);
(Continued)

(58) Field of Classification Search
CPC ............ A61F 13/0213; A61F 13/00063; A61F 13/36; A61F 13/0206; A61F 2013/0094; A61F 2013/00523; A61F 2013/00748; A61F 13/0223; A61F 13/0226; A61F 13/38; A61L 15/60; A61L 15/46; A61L 15/28; A61L 15/425; A61L 15/48; A61L 15/56; A61L 2300/404; A61L 15/22;
(Continued)

(56) References Cited

U.S. PATENT DOCUMENTS 10,016,537 B2 7/2018 Menon et al.
10,046,096 B2 8/2018 Askem et al.
(Continued)

FOREIGN PATENT DOCUMENTS

CN 102057275 A 5/2011
CN 103874516 A 6/2014
(Continued)

OTHER PUBLICATIONS

International Search Report and Written Opinion for PCT/IB2020/000444; issued Sep. 22, 2020; 15 pages.
(Continued)

*Primary Examiner* — Susan S Su
*Assistant Examiner* — Meagan Ngo
(74) *Attorney, Agent, or Firm* — TAFT STETTINIUS & HOLLISTER LLP; Ryan O. White; Derek B. Lavender

(57) ABSTRACT

Provided herein are fabric materials and debridement devices comprising gel-forming hydrofibres for disrupting a biofilm, loosening, or sequestering unwanted materials from wounds, and uses thereof. In particular, debridement and detection devices for selective and atraumatic removal of unwanted tissues and for detection of a wound infection are provided.

22 Claims, 8 Drawing Sheets

(51) Int. Cl.
*A61F 13/0206* (2024.01)
*A61L 15/28* (2006.01)
*A61L 15/42* (2006.01)
*A61L 15/48* (2006.01)
*A61L 15/56* (2006.01)
*A61L 15/60* (2006.01)

(52) U.S. Cl.
CPC ...... *A61F 13/0223* (2013.01); *A61F 13/0226* (2013.01); *A61L 15/28* (2013.01); *A61L 15/425* (2013.01); *A61L 15/48* (2013.01); *A61L 15/56* (2013.01); *A61L 15/60* (2013.01); *A61F 2013/0094* (2013.01); *A61L 2300/404* (2013.01)

(58) Field of Classification Search
CPC ............. A61L 15/42; A46B 2200/1006; A46B 2200/10; A46B 3/00; A61B 2017/320012; C12Q 1/04
See application file for complete search history.

(56) References Cited

U.S. PATENT DOCUMENTS

| | | |
|---|---|---|
| 10,076,447 B2 | 9/2018 | Barta et al. |
| 10,076,587 B2 | 9/2018 | Locke et al. |
| 10,143,784 B2 | 12/2018 | Walton et al. |
| 10,426,670 B2 | 10/2019 | von Blucher et al. |
| 10,426,747 B2 | 10/2019 | Johnson |
| 10,426,874 B2 | 10/2019 | Chien et al. |
| 10,426,875 B2 | 10/2019 | Blott et al. |
| 10,426,938 B2 | 10/2019 | Locke et al. |
| 10,434,015 B2 | 10/2019 | Taylor et al. |
| 10,434,142 B2 | 10/2019 | Niazi et al. |
| 10,434,210 B2 | 10/2019 | Olson et al. |
| 10,434,284 B2 | 10/2019 | Hanson et al. |
| 10,449,094 B2 | 10/2019 | Donda et al. |
| D866,756 S | 11/2019 | Allen et al. |
| 10,463,760 B2 | 11/2019 | Karthikeyan et al. |
| 10,463,773 B2 | 11/2019 | Haggstrom et al. |
| 10,470,933 B2 | 11/2019 | Riesinger |
| 10,470,936 B2 | 11/2019 | Wohlgemuth et al. |
| 10,471,122 B2 | 11/2019 | Shi et al. |
| 10,471,190 B2 | 11/2019 | Locke et al. |
| 10,478,345 B2 | 11/2019 | Barta et al. |
| 10,478,346 B2 | 11/2019 | Knutson |
| 10,478,394 B2 | 11/2019 | Yu |
| 10,485,707 B2 | 11/2019 | Sexton |
| 10,485,891 B2 | 11/2019 | Andrews et al. |
| 10,485,892 B2 | 11/2019 | Hands et al. |
| 10,485,906 B2 | 11/2019 | Freedman et al. |
| 10,486,135 B2 | 11/2019 | Yang et al. |
| 10,492,956 B2 | 12/2019 | Zamierowski |
| 10,493,178 B2 | 12/2019 | Marchant et al. |
| 10,493,184 B2 | 12/2019 | Collinson et al. |
| 10,493,185 B2 | 12/2019 | Stokes et al. |
| 10,500,099 B2 | 12/2019 | Hung et al. |
| 10,500,103 B2 | 12/2019 | Croizat et al. |
| 10,500,104 B2 | 12/2019 | Sookraj |
| 10,500,173 B2 | 12/2019 | Yang et al. |
| 10,500,235 B2 | 12/2019 | Wardell |
| 10,500,300 B2 | 12/2019 | Dybe et al. |
| 10,500,301 B2 | 12/2019 | Laurensou |
| 10,500,302 B2 | 12/2019 | Holm et al. |
| 10,501,487 B2 | 12/2019 | Andrews et al. |
| 10,506,928 B2 | 12/2019 | Locke et al. |
| 10,507,141 B2 | 12/2019 | Allen et al. |
| 10,507,259 B2 | 12/2019 | Cree et al. |
| 10,512,707 B2 | 12/2019 | Whalen, III et al. |
| 10,525,170 B2 | 1/2020 | Havenstrite et al. |
| 10,532,137 B2 | 1/2020 | Pratt et al. |
| 10,532,194 B2 | 1/2020 | Locke et al. |
| 10,537,657 B2 | 1/2020 | Phillips et al. |
| 10,542,936 B2 | 1/2020 | Goldberg et al. |
| 10,543,133 B2 | 1/2020 | Shaw et al. |
| 10,543,293 B2 | 1/2020 | Suschek |
| 10,548,777 B2 | 2/2020 | Locke et al. |
| 10,549,008 B2 | 2/2020 | Yoo |
| 10,549,016 B2 | 2/2020 | Bushko et al. |
| 10,549,017 B2 | 2/2020 | Hsiao et al. |
| 10,555,838 B2 | 2/2020 | Wu et al. |
| 10,555,839 B2 | 2/2020 | Hartwell |
| 10,556,044 B2 | 2/2020 | Robinson et al. |
| 10,561,533 B2 | 2/2020 | Hoggarth et al. |
| 10,561,536 B2 | 2/2020 | Holm et al. |
| 10,568,767 B2 | 2/2020 | Addison et al. |
| 10,568,768 B2 | 2/2020 | Long et al. |
| 10,568,770 B2 | 2/2020 | Robinson et al. |
| 10,568,771 B2 | 2/2020 | MacDonald et al. |
| 10,568,773 B2 | 2/2020 | Tuck et al. |
| 10,568,983 B2 | 2/2020 | Gerdes et al. |
| 10,575,991 B2 | 3/2020 | Dunn |
| 10,575,992 B2 | 3/2020 | Sarangapani et al. |
| 10,576,037 B2 | 3/2020 | Harrell |
| 10,576,189 B2 | 3/2020 | Locke et al. |
| 10,583,042 B2 | 3/2020 | Sarangapani et al. |
| 10,583,228 B2 | 3/2020 | Shuler et al. |
| 10,589,007 B2 | 3/2020 | Coulthard et al. |
| 10,590,184 B2 | 3/2020 | Kuo |
| 10,610,414 B2 | 4/2020 | Hartwell et al. |
| 10,610,415 B2 | 4/2020 | Griffey et al. |
| 10,610,623 B2 | 4/2020 | Robinson et al. |
| 10,617,569 B2 | 4/2020 | Bonn |
| 10,617,608 B2 | 4/2020 | Shin et al. |
| 10,617,769 B2 | 4/2020 | Huang |
| 10,617,784 B2 | 4/2020 | Yu et al. |
| 10,617,786 B2 | 4/2020 | Kluge et al. |
| 10,618,266 B2 | 4/2020 | Wright et al. |
| 10,624,984 B2 | 4/2020 | Courage et al. |
| 10,625,002 B2 | 4/2020 | Locke et al. |
| 10,632,019 B2 | 4/2020 | Vitaris |
| 10,632,224 B2 | 4/2020 | Hardy et al. |
| 10,639,206 B2 | 5/2020 | Hu et al. |
| 10,639,350 B2 | 5/2020 | Arber et al. |
| 10,639,404 B2 | 5/2020 | Lichtenstein |
| 10,646,614 B2 | 5/2020 | Grinstaff et al. |
| 10,653,562 B2 | 5/2020 | Robinson et al. |
| 10,653,782 B2 | 5/2020 | Ameer et al. |
| 10,653,810 B2 | 5/2020 | Datt et al. |
| 10,653,821 B2 | 5/2020 | Nichols |
| 10,653,823 B2 | 5/2020 | Bharti et al. |
| 10,660,799 B2 | 5/2020 | Wu et al. |
| 10,660,851 B2 | 5/2020 | Millis et al. |
| 10,660,992 B2 | 5/2020 | Canner et al. |
| 10,660,994 B2 | 5/2020 | Askem et al. |
| 10,667,955 B2 | 6/2020 | Allen et al. |
| 10,667,956 B2 | 6/2020 | Van Holten et al. |
| 10,682,257 B2 | 6/2020 | Lu |
| 10,682,258 B2 | 6/2020 | Manwaring et al. |
| 10,682,259 B2 | 6/2020 | Hunt et al. |
| 10,682,318 B2 | 6/2020 | Twomey et al. |
| 10,682,386 B2 | 6/2020 | Ellis-Behnke et al. |
| 10,682,446 B2 | 6/2020 | Askem et al. |
| 10,687,983 B2 | 6/2020 | Dahlberg et al. |
| 10,687,985 B2 | 6/2020 | Lee et al. |
| 10,688,215 B2 | 6/2020 | Munro et al. |
| 10,688,217 B2 | 6/2020 | Hanson et al. |
| RE48,117 E | 7/2020 | Albert et al. |
| 10,702,419 B2 | 7/2020 | Locke et al. |
| 10,702,420 B2 | 7/2020 | Hammond et al. |
| 10,703,942 B2 | 7/2020 | Tunius |
| 10,709,760 B2 | 7/2020 | Gronberg et al. |
| 10,709,807 B2 | 7/2020 | Kshirsagar |
| 10,709,883 B2 | 7/2020 | Spector |
| 10,716,711 B2 | 7/2020 | Locke et al. |
| 10,716,874 B2 | 7/2020 | Koyama et al. |
| 10,729,589 B2 | 8/2020 | Dorian et al. |
| 10,729,590 B2 | 8/2020 | Simmons et al. |
| 10,729,826 B2 | 8/2020 | Lin |
| 10,736,787 B2 | 8/2020 | Hannigan et al. |
| 10,736,788 B2 | 8/2020 | Locke et al. |
| 10,736,985 B2 | 8/2020 | Odermatt et al. |
| 10,737,003 B2 | 8/2020 | Fujisaki |
| 10,743,900 B2 | 8/2020 | Ingram et al. |

(56) References Cited

U.S. PATENT DOCUMENTS

| | | |
|---|---|---|
| 10,744,040 B2 | 8/2020 | Kazala, Jr. et al. |
| 10,744,041 B2 | 8/2020 | Hartwell |
| 10,744,225 B2 | 8/2020 | Lindgren et al. |
| 10,744,237 B2 | 8/2020 | Guidi et al. |
| 10,744,238 B2 | 8/2020 | Guidi et al. |
| 10,744,239 B2 | 8/2020 | Armstrong et al. |
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 11,026,847 B2 | 6/2021 | Piotrowski et al. |
| 11,058,588 B2 | 7/2021 | Albert et al. |
| 11,076,997 B2 | 8/2021 | Hunt et al. |
| 11,123,215 B2 | 9/2021 | Pradhan |
| 11,147,714 B2 | 10/2021 | Blott et al. |
| 11,154,426 B2 | 10/2021 | Riesinger |
| 11,191,810 B2 | 12/2021 | Gronberg et al. |
| 11,229,719 B2 | 1/2022 | Locke et al. |
| 11,238,756 B2 | 2/2022 | Carroll et al. |
| 11,246,761 B2 | 2/2022 | Holm et al. |
| 11,247,034 B2 | 2/2022 | Armstrong et al. |
| 11,259,528 B2 | 3/2022 | Ingram et al. |
| 11,266,537 B2 | 3/2022 | Robinson et al. |
| 11,273,077 B2 | 3/2022 | Kubek |
| 11,278,658 B2 | 3/2022 | Haggstrom et al. |
| 11,291,746 B2 | 4/2022 | Chakravarthy et al. |
| 2006/0155260 A1 | 7/2006 | Blott et al. |
| 2006/0172000 A1 | 8/2006 | Cullen et al. |
| 2007/0185426 A1 | 8/2007 | Ambrosio et al. |
| 2007/0219512 A1 | 9/2007 | Heaton et al. |
| 2007/0239078 A1 | 10/2007 | Jaeb |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0217357 A1* | 8/2010 | Da Silva ............... A61K 8/368 132/212 |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0046670 A1* | 2/2012 | Engl ............... A61F 13/00017 112/475.01 |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0101165 A1 | 4/2016 | Salamone et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0151314 A1 | 6/2017 | Salamone et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |

(56) References Cited

U.S. PATENT DOCUMENTS

| | | |
|---|---|---|
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 * | 5/2019 | Bishop ............... A61F 13/0216 |
| 2019/0142642 A1 | 5/2019 | Burnet |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0224363 A1 * | 7/2019 | Gerdes ............... A61B 5/6833 |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282247 A1 * | 9/2019 | Shelton ............... A61B 17/221 |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000643 A1 | 1/2020 | Locke |
| 2020/0000955 A1 | 1/2020 | Andrews et al. |
| 2020/0000956 A1 | 1/2020 | Huang et al. |
| 2020/0000960 A1 | 1/2020 | Kellar et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |

(56) References Cited

U.S. PATENT DOCUMENTS

| | | |
|---|---|---|
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0100945 A1 | 4/2020 | Albert et al. |
| 2020/0101192 A1 | 4/2020 | Folwarzny |
| 2020/0107964 A1 | 4/2020 | Locke et al. |
| 2020/0107965 A1 | 4/2020 | Greener |
| 2020/0107966 A1 | 4/2020 | Francis |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121509 A1 | 4/2020 | Locke et al. |
| 2020/0121510 A1 | 4/2020 | Hartwell et al. |
| 2020/0121513 A1 | 4/2020 | Townsend et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129648 A1 | 4/2020 | Drury et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139002 A1 | 5/2020 | Dudnyk et al. |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0146896 A1 | 5/2020 | Rice et al. |
| 2020/0146897 A1 | 5/2020 | Locke et al. |
| 2020/0146899 A1 | 5/2020 | Pratt et al. |
| 2020/0155355 A1 | 5/2020 | Hill et al. |
| 2020/0155358 A1 | 5/2020 | Wheldrake |
| 2020/0155359 A1 | 5/2020 | Carroll et al. |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179300 A1 | 6/2020 | Urban et al. |
| 2020/0179558 A1 | 6/2020 | Munro et al. |
| 2020/0179673 A1 | 6/2020 | Wan |
| 2020/0188179 A1 | 6/2020 | Bugedo-Albizuri et al. |
| 2020/0188180 A1 | 6/2020 | Akbari et al. |
| 2020/0188182 A1 | 6/2020 | Sanders et al. |
| 2020/0188183 A1 | 6/2020 | Hamerslagh et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1* | 6/2020 | Locke ............... A61F 13/00068 |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206035 A1 | 7/2020 | Kantor et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0214899 A1 | 7/2020 | Locke et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0230283 A1 | 7/2020 | Yang et al. |
| 2020/0237562 A1 | 7/2020 | Rice et al. |
| 2020/0237564 A1 | 7/2020 | Hammond et al. |
| 2020/0237816 A1 | 7/2020 | Lait |
| 2020/0246190 A1 | 8/2020 | Luckemeyer et al. |
| 2020/0246191 A1 | 8/2020 | Lu et al. |
| 2020/0246194 A1 | 8/2020 | Gonzalez et al. |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0253788 A1 | 8/2020 | Rehbein et al. |
| 2020/0254139 A1 | 8/2020 | Phillips et al. |
| 2020/0261275 A1 | 8/2020 | Manwaring et al. |
| 2020/0261276 A1 | 8/2020 | Hemandez et al. |
| 2020/0268560 A1 | 8/2020 | Harrison et al. |
| 2020/0268561 A1 | 8/2020 | Locke et al. |
| 2020/0269028 A1 | 8/2020 | Hegg |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289326 A1 | 9/2020 | Nielsen et al. |
| 2020/0289327 A1 | 9/2020 | Hansen et al. |
| 2020/0289328 A1 | 9/2020 | Luckemeyer et al. |
| 2020/0289346 A1 | 9/2020 | Hansen et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory et al. |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306092 A1 | 10/2020 | Rehbein et al. |
| 2020/0306094 A1 | 10/2020 | Kushnir et al. |
| 2020/0306426 A1 | 10/2020 | Rice et al. |
| 2020/0306428 A1 | 10/2020 | Ingram et al. |
| 2020/0306430 A1 | 10/2020 | Rehbein et al. |
| 2020/0315853 A1 | 10/2020 | Waite |
| 2020/0315854 A1 | 10/2020 | Simmons et al. |
| 2020/0315894 A1 | 10/2020 | Churilla et al. |
| 2020/0316271 A1 | 10/2020 | Lin |
| 2020/0316272 A1 | 10/2020 | Simpson |
| 2020/0316273 A1 | 10/2020 | Hegg |

(56) References Cited

U.S. PATENT DOCUMENTS

| | | |
|---|---|---|
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |
| 2021/0007764 A1* | 1/2021 | Wilhelms ............ D04H 3/10 |
| 2021/0177660 A1 | 6/2021 | Rapp |
| 2021/0196310 A1 | 7/2021 | Moore et al. |
| 2021/0205142 A1 | 7/2021 | Rice et al. |
| 2021/0228416 A1 | 7/2021 | Eriksson et al. |
| 2021/0228786 A1 | 7/2021 | Perry |
| 2021/0244431 A1 | 8/2021 | Hentrich et al. |
| 2021/0290815 A1 | 9/2021 | Parsons et al. |
| 2021/0322666 A1 | 10/2021 | Greener |
| 2021/0330855 A1 | 10/2021 | Waite et al. |
| 2021/0338486 A1 | 11/2021 | Dagger et al. |
| 2021/0338489 A1 | 11/2021 | Hunt et al. |
| 2021/0361820 A1 | 11/2021 | Bourdillon et al. |
| 2021/0378876 A1 | 12/2021 | Gowans |
| 2021/0402049 A1 | 12/2021 | Waite et al. |
| 2022/0001212 A1 | 1/2022 | Bass et al. |
| 2022/0031231 A1 | 2/2022 | Hunt et al. |
| 2022/0087869 A1 | 3/2022 | Wheldrake |
| 2022/0105231 A1 | 4/2022 | Locke et al. |
| 2022/0117794 A1 | 4/2022 | Hartwell et al. |
| 2022/0142820 A1 | 5/2022 | Delury et al. |
| 2022/0143297 A1 | 5/2022 | Gowans et al. |

FOREIGN PATENT DOCUMENTS

| | | |
|---|---|---|
| CN | 109310528 A | 2/2019 |
| EP | 0788378 B1 | 2/2003 |
| EP | 3187204 A1 | 7/2017 |
| EP | 3250244 B8 | 12/2017 |
| EP | 3556407 A1 | 10/2019 |
| EP | 3569260 A1 | 11/2019 |
| EP | 3622975 A1 | 3/2020 |
| EP | 3643328 A1 | 4/2020 |
| EP | 3643330 A1 | 4/2020 |
| EP | 3643331 A1 | 4/2020 |
| EP | 3669838 A1 | 6/2020 |
| EP | 3669843 A1 | 6/2020 |
| EP | 3669844 A1 | 6/2020 |
| EP | 3834787 A1 | 6/2021 |
| EP | 3836872 A1 | 6/2021 |
| EP | 3849626 A1 | 7/2021 |
| EP | 3858392 A1 | 8/2021 |
| EP | 3860664 A1 | 8/2021 |
| EP | 3866920 A1 | 8/2021 |
| EP | 3630031 B1 | 9/2021 |
| EP | 3876240 A1 | 9/2021 |
| EP | 3876885 A1 | 9/2021 |
| EP | 3876886 A1 | 9/2021 |
| EP | 2948116 B1 | 10/2021 |
| EP | 3908240 A1 | 11/2021 |
| EP | 3681452 B1 | 12/2021 |
| EP | 3914208 A1 | 12/2021 |
| EP | 3672655 B1 | 1/2022 |
| EP | 3142615 B1 | 2/2022 |
| EP | 3687467 B1 | 2/2022 |
| EP | 3801662 B1 | 2/2022 |
| EP | 3946498 A1 | 2/2022 |
| EP | 3952809 A1 | 2/2022 |
| EP | 3965835 A1 | 3/2022 |
| EP | 3969072 A1 | 3/2022 |
| EP | 3586805 B1 | 4/2022 |
| EP | 3982896 A1 | 4/2022 |
| EP | 3989897 A1 | 5/2022 |
| EP | 3999006 A1 | 5/2022 |
| EP | 3703633 B1 | 6/2022 |
| EP | 4007550 A1 | 6/2022 |
| EP | 4007552 A1 | 6/2022 |
| EP | 4009929 A1 | 6/2022 |
| GB | 2579211 A | 6/2020 |
| GB | 2579368 A | 6/2020 |
| GB | 2592804 A | 9/2021 |
| GB | 2592805 A | 9/2021 |
| GB | 2592806 A | 9/2021 |
| GB | 2593114 A | 9/2021 |
| WO | 2005018543 A2 | 3/2005 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |

(56) References Cited

FOREIGN PATENT DOCUMENTS

| | | | |
|---|---|---|---|
| WO | 2020043665 | A1 | 3/2020 |
| WO | 2020044237 | A1 | 3/2020 |
| WO | 2020046443 | A1 | 3/2020 |
| WO | 2020047255 | A1 | 3/2020 |
| WO | 2020049038 | A1 | 3/2020 |
| WO | 2020055945 | A1 | 3/2020 |
| WO | 2020056014 | A1 | 3/2020 |
| WO | 2020056182 | A1 | 3/2020 |
| WO | 2020065531 | A1 | 4/2020 |
| WO | 2020070231 | A1 | 4/2020 |
| WO | 2020074512 | A1 | 4/2020 |
| WO | 2020078993 | A1 | 4/2020 |
| WO | 2020079009 | A1 | 4/2020 |
| WO | 2020079330 | A1 | 4/2020 |
| WO | 2020081259 | A1 | 4/2020 |
| WO | 2020081391 | A1 | 4/2020 |
| WO | 2020092598 | A1 | 5/2020 |
| WO | 2020136555 | A1 | 7/2020 |
| WO | 2020141059 | A1 | 7/2020 |
| WO | 2020144347 | A1 | 7/2020 |
| WO | 2020150548 | A1 | 7/2020 |
| WO | 2020159675 | A1 | 8/2020 |
| WO | 2020159677 | A1 | 8/2020 |
| WO | 2020159678 | A1 | 8/2020 |
| WO | 2020159823 | A1 | 8/2020 |
| WO | 2020159859 | A1 | 8/2020 |
| WO | 2020159892 | A1 | 8/2020 |
| WO | 2020161086 | A1 | 8/2020 |
| WO | 2020173665 | A1 | 9/2020 |
| WO | 2020173760 | A1 | 9/2020 |
| WO | 2020174264 | A1 | 9/2020 |
| WO | 2020174510 | A1 | 9/2020 |
| WO | 2020182887 | A1 | 9/2020 |
| WO | 2020185810 | A1 | 9/2020 |
| WO | 2020197759 | A1 | 10/2020 |
| WO | 2020197760 | A1 | 10/2020 |
| WO | 2020198484 | A1 | 10/2020 |
| WO | 2020201879 | A1 | 10/2020 |
| WO | 2020213998 | A1 | 10/2020 |

OTHER PUBLICATIONS

Chinese Office Action; China National Intellectual Property Administration; Chinese Patent Application No. 202080040454.5; May 7, 2022; 11 pages.

* cited by examiner

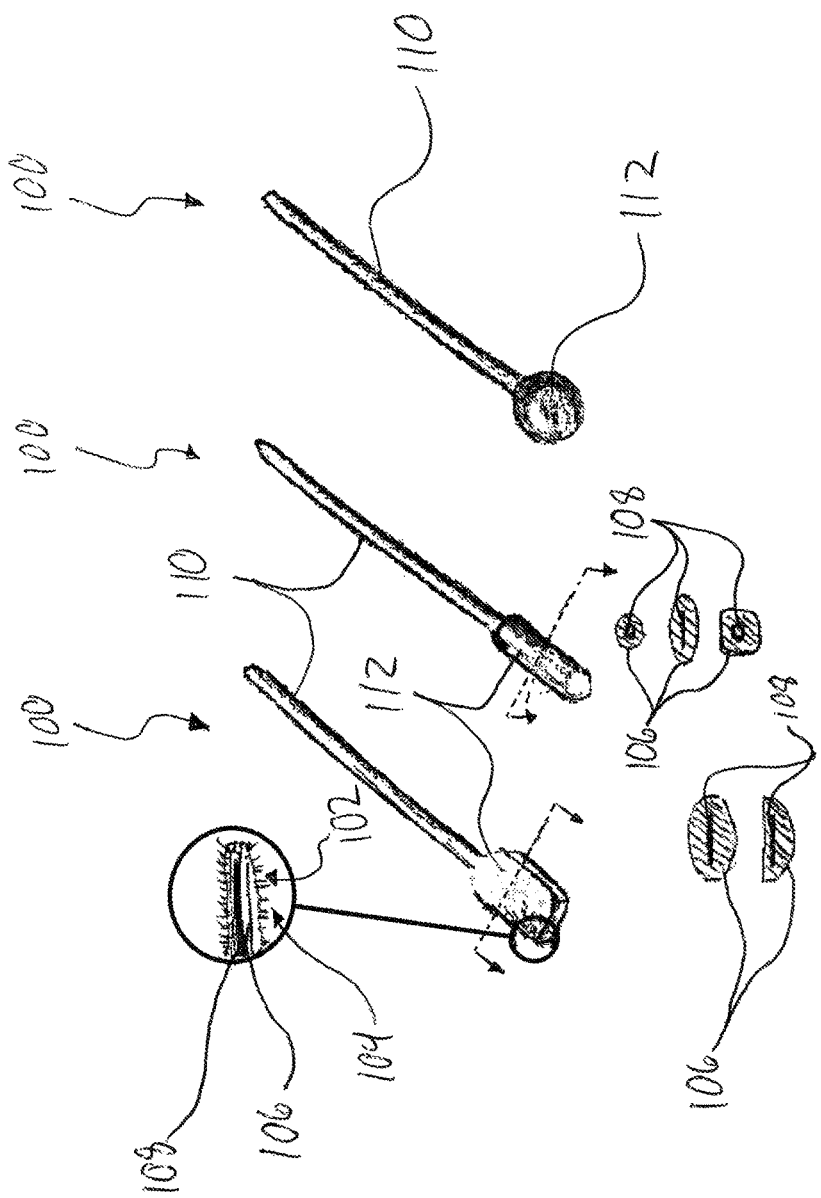

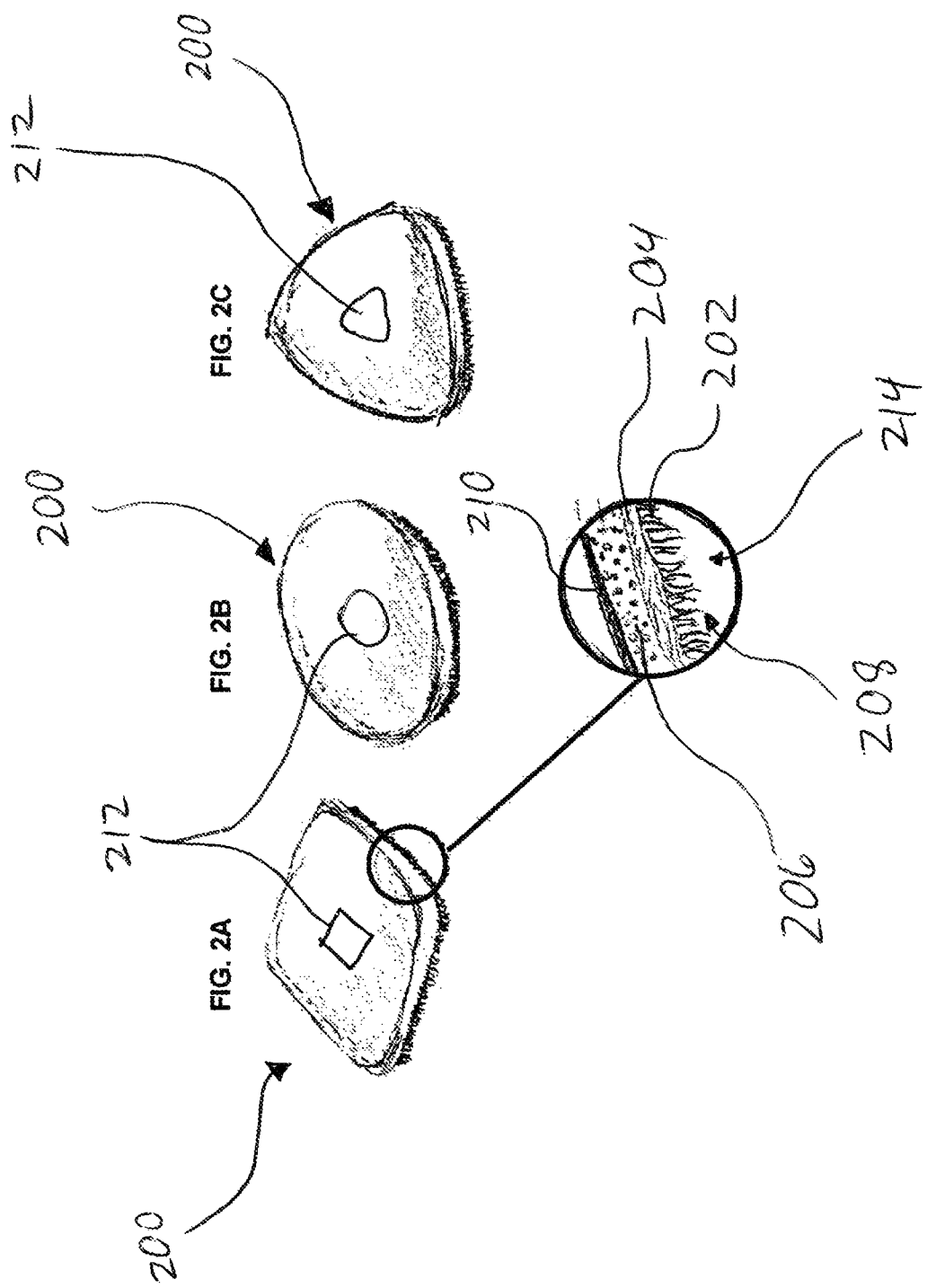

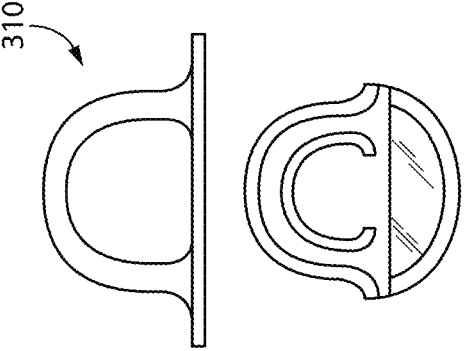
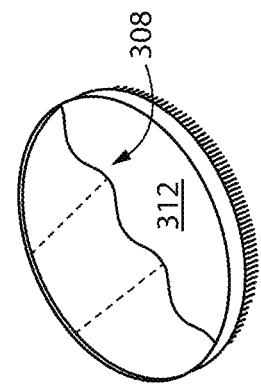
FIG. 3B
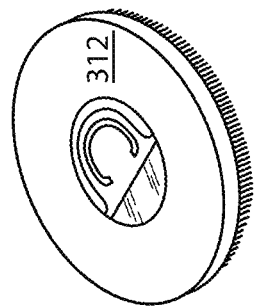
FIG. 3D
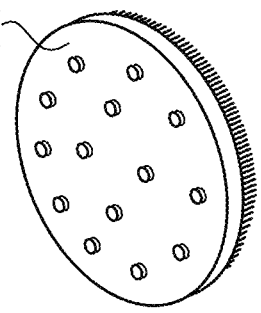
FIG. 3F
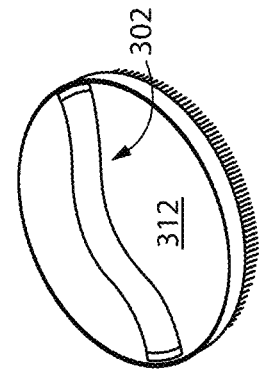
FIG. 3A
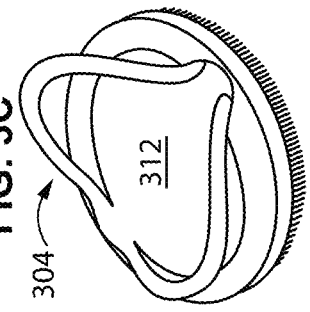
FIG. 3C
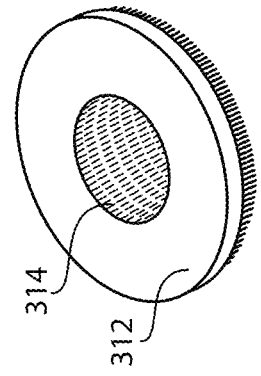
FIG. 3E

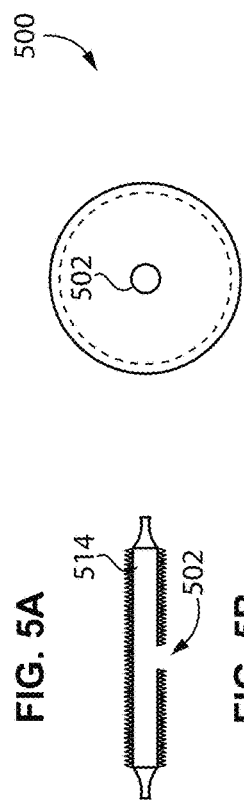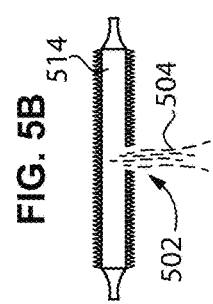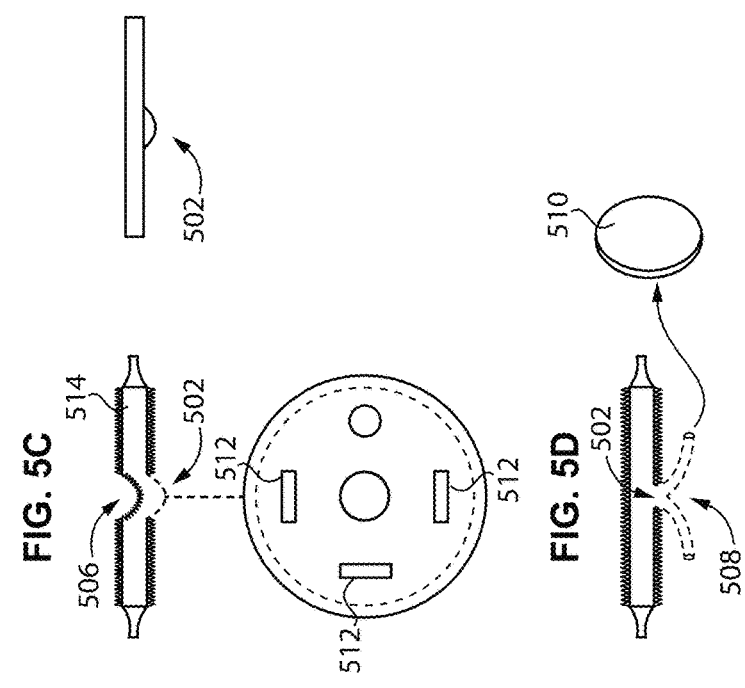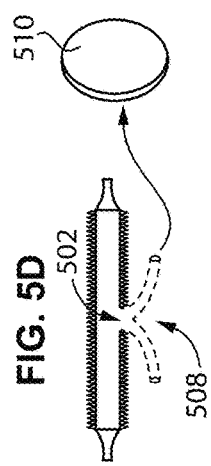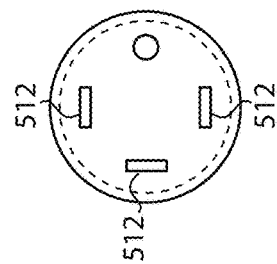

METHODS AND DEVICES TO DISRUPT AND CONTAIN PATHOGENS

CROSS-REFERENCE TO RELATED APPLICATION

This application claims the benefit of U.S. Provisional Application No. 62/856,676 filed on Jun. 3, 2019, the contents of which are incorporated herein in entirety.

BACKGROUND

In mammals, injury triggers an organized complex cascade of cellular and biochemical events that result in a healed wound. Wound healing is a complex dynamic process that results in the restoration of anatomic continuity and function: an ideally healed wound is one that has returned to normal anatomic structure, function, and appearance. Infection of the wound results in either a slower or an arrested healing process. Pathogens in a wound can produce toxins (e.g., *Clostridium* spp), noxious metabolites like ammonia that raise pH (e.g., *Proteus* spp), tissue-lytic enzymes like proteases, or further invade tissue by other means leading to an increase in wound area. In a worst case, pathogens can leave the wound and cause sepsis.

Unwanted biological soft tissues such as devitalized tissue (e.g. slough, necrosis, eschar) or exogenous tissues (e.g. microbial biofilm) are a significant source of soft tissue infections. Removal of such unwanted tissues from surgical or chronic wounds, for example, is vital to help prevent infection and allow the site or wound to heal. Such tissue removal (debridement) is achieved by various methods such as surgical debridement, sharp debridement, use of digesting enzymes, and biosurgery.

Antimicrobial agents, including antiseptics and antibiotics, are widely used to treat microbial infections. However, the emergence of antibiotic resistance and the ability of microorganisms to tolerate antimicrobial agents through their production of protective biofilm have significantly reduced their effectiveness. Therefore, new ways to disturb microbial habitats by disrupting biofilm, for example, increase susceptibility of microorganisms to antimicrobial agents, and develop alternative strategies to antimicrobial agents are required. Moreover, because conventional methods of debridement often cause pain and trauma, alternative methods that are effective but also less traumatic and painful are required.

SUMMARY

Disclosed herein are devices, methods and kits for debridement of a wound, comprising a wound contacting layer with a plurality of bristles in contact with a layer of gel-forming fibres. In some embodiments, the plurality of bristles comprises a pile of monofilaments or fibres. In some embodiments, the monofilaments comprise nylon, acetal, polypropylene, acrylic, polyvinyl chloride (PVC), polycarbonate, silicone, wool, or any combination thereof. In yet other embodiments, the bristles comprise a pile of nylon monofilaments. In still other embodiments, the bristles comprise nonwoven or woven filaments arranged perpendicular to the wound contacting layer.

In some embodiments, the layer of gel-forming fibres are woven, non-woven, and/or knitted. In yet other embodiments, the layer of gel-forming fibres is selected from the group consisting of sodium carboxymethylcellulose, alginate, cellulose, carboxyethylcellulose, cellulose ethyl sulfonate, modified cellulose, pectin, chitosan, modified chitosan, hyaluronic acid, polysaccharide, gum-derived polymer, and any combination thereof. In yet other embodiments, the layer of gel-forming fibres comprises sodium carboxymethylcellulose. In some embodiments, the layer of gel-forming fibres has an absorbency of at least 10 g/g and resists lateral spread of a fluid upon absorption. In other embodiments, the layer of gel-forming fibres has an absorbency of 15 g/g to 50 g/g and resists lateral spread of a fluid upon absorption. In yet other embodiments, the carboxymethylcellulose has a degree of substitution of at least 0.05 carboxymethyl groups per cellulose unit. In still other embodiments, the carboxymethylcellulose has a degree of substitution of at least 0.2 carboxymethyl groups per cellulose unit. In yet other embodiments, the carboxymethylcellulose has a degree of substitution of between 0.3 and 0.5 carboxymethyl groups per cellulose unit.

In some embodiments, the devices, methods and kits for debridement disclosed herein are capable of disrupting a biofilm on a wound. In some embodiments, the devices and methods for debridement disclosed herein are capable of sequestering metal ions. In some embodiments, the devices and methods for debridement disclosed herein further comprise anti-biofilm agents, metal chelators, surfactants, or any combination thereof. In other embodiments, the devices and methods for debridement disclosed herein are capable of removing or loosening unwanted tissue or biofilm on a wound. In yet other embodiments, the devices and methods for debridement disclosed herein are capable of sequestering bacteria and other components of a biofilm or unwanted tissue.

In some embodiments, the devices, methods and kits for debridement disclosed herein further comprise one or more support layers in contact with the layer of gel-forming fibres, wherein the support layer comprises foam, fabric, blended fabric, paper, polymer, plastic, or any combination thereof. In some embodiments, the one or more support layers form a backing. In yet other embodiments, an outer support layer comprises an anti-slip material. In still other embodiments, the anti-slip material comprises silicone.

In other embodiments, the devices, methods and kits disclosed herein further comprise a diagnostic unit in fluid communication with the layer of gel-forming fibres. In some embodiments, the diagnostic unit comprises an enzyme-based assay or an electronic sensor. In other embodiments, the diagnostic unit comprises one or more fibres or diagnostic disks, comprising: a) a reaction layer comprising one or more reagents that interact with a target enzyme indicative of a microbial infection, wherein the reagents are affixed to a solid phase; b) each reagent is sprayed, printed, or deposited in a reagent area separated by impermeable separators; c) each reagent area comprises a reporter area wherein a color, color change, or other detectable signal is observed; and d) a transparent cover comprising a window for visualizing the signal in the reporter area. In some embodiments, the fluid communication comprises a wicking material, an opening, a channel, or a conduit. In yet other embodiments, the wicking material comprises hydrophilic fibres, gelling fibres, filter paper, or any combination thereof. In some embodiments, the diagnostic disks comprise one or more reagents selected from the group consisting of enzyme-reactive indicators, enzymes that produce colored products, pH indicators, protein responsive reagents, and moisture-detecting reagents. In other embodiments, the enzyme-reactive indicators interact with one or more enzymes selected from the group consisting of elastase, lysozyme, cathepsin G, myeloperoxidase, and any combination thereof to produce a visible color or an electronic change in the reporter area of the diagnostic disk.

In some embodiments, the devices, methods and kits disclosed herein further comprise a handle attached to a non-wound-contacting surface of the debridement device. In some embodiments, the handle comprises a loop, a stick, a tube, a tab, a bar, a pocket, a fold, a sleeve, or a protrusion on the non-wound-contacting surface. In other embodiments, the handle is removably attached to the non-wound-contacting surface using a detachable securing member. In yet other embodiments, the detachable securing member comprises a hook-and-loop element, an adhesive, or a sticker.

Disclosed herein are devices, methods and kits for detecting a wound infection, comprising debriding a wound using the debridement devices described herein, extracting a sample of wound tissue from the debridement device, and analyzing the sample for presence of a microbial infection using a diagnostic assay. In some embodiments, the diagnostic assay comprises PCR, enzyme-linked immunosorbent assay (ELISA), or an immunoassay. In other embodiments, the immunoassay comprises one or more reagents selected from the group consisting of enzyme-reactive indicators, enzymes that produce colored products, pH indicators, protein responsive reagents, and moisture-detecting reagents, and wherein the enzyme-reactive indicators interact with one or more enzymes selected from the group consisting of elastase, lysozyme, cathepsin G, myeloperoxidase, and any combination thereof to produce a detectable signal indicative of a microbial infection.

Disclosed herein are methods, devices and kits for treating a wound, comprising cleaning a wound using a debridement device as described herein, analyzing a wound sample removed by the debridement device for presence of a microbial infection using a diagnostic assay; and applying a wound dressing comprising gel-forming fibres with or without an antimicrobial agent according to a result of the diagnostic assay. In some embodiments, the diagnostic assay comprises one or more diagnostic disks in fluid communication with the debridement device, a standalone immunoassay, PCR, or ELISA. In yet other embodiments, the diagnostic disks comprise: a) a reaction layer comprising one or more reagents that interact with a target enzyme indicative of a microbial infection, wherein the reagents are affixed to a solid phase; b) each reagent is sprayed, printed, or deposited in a reagent area separated by impermeable separators; c) each reagent area comprises a reporter area wherein a color, color change, or other detectable signal is observed; and d) a transparent cover comprising a window for visualizing the signal in the reporter area. In some embodiments, the fluid communication comprises a wicking material, an opening, a channel, or a conduit. In other embodiments, the wicking material comprises hydrophilic fibres, gelling fibres, or filter paper. In yet other embodiments, the diagnostic disks comprise one or more reagents selected from the group consisting of enzyme-reactive indicators, enzymes that produce colored products, pH indicators, protein responsive reagents, and moisture-detecting reagents. In still other embodiments, the enzyme-reactive indicators interact with one or more enzymes selected from the group consisting of elastase, lysozyme, cathepsin G, myeloperoxidase, and any combination thereof to produce a visible color or an electronic change in the reporter area of the diagnostic disk.

Disclosed herein are devices, methods and kits for debridement of a wound, comprising a wound contacting layer with a plurality of nylon monofilaments or bristles in contact with a layer of gel-forming fibres comprising carboxymethylcellulose. In some embodiments, the layer of gel-forming fibres has an absorbency of at least 10 g/g and resists lateral spread of a fluid upon absorption. In yet other embodiments, the devices and methods for debridement of a wound as disclosed herein are capable of disrupting a biofilm, or loosening or removing unwanted tissue on a wound. In yet other embodiments, the devices and methods for debridement disclosed herein are capable of sequestering metal ions, bacteria, and/or unwanted wound tissue. In still other embodiments, the devices and methods for debridement disclosed herein comprise anti-biofilm agents, metal chelators, surfactants, or any combination thereof.

In some embodiments, the devices, methods and kits for debridement disclosed herein further comprise a handle attached to a non-wound-contacting surface of the debridement device. In some embodiments, the handle comprises a loop, a stick, a tube, a tab, a bar, a pocket, a fold, a sleeve, a protrusion on the non-wound-contacting surface, or a detachable bar or stick. In some embodiments, the devices and methods for debridement disclosed herein further comprise one or more diagnostic disks in fluid communication with the debridement device, comprising: a) a reaction layer comprising one or more reagents that interact with a target enzyme indicative of a microbial infection, wherein the reagents are affixed to a solid phase; b) each reagent is sprayed, printed, or deposited in a reagent area separated by impermeable separators; c) each reagent area comprises a reporter area wherein a color, color change, or other detectable signal is observed; and d) a transparent cover comprising a window for visualizing the signal in the reporter area. In some embodiments, the fluid communication comprises wicking fibres, an opening, or a filter paper. In other embodiments, one or more reagents in conjunction with the devices and methods for debridement disclosed herein are selected from the group consisting of enzyme-reactive indicators, enzymes that produce colored products, pH indicators, protein responsive reagents, and moisture-detecting reagents, and wherein the enzyme-reactive indicators interact with one or more enzymes selected from the group consisting of elastase, lysozyme, cathepsin G, myeloperoxidase, and any combination thereof to produce a detectable signal indicative of a microbial infection.

Disclosed herein are methods, devices and kits for disrupting a biofilm or removing unwanted tissue on a wound, comprising debriding a wound using the devices for debridement disclosed herein.

Also disclosed herein are methods, devices and kits for treating a wound, comprising debriding a wound using the debridement device as described herein; analyzing a wound sample adsorbed to the debridement device using a diagnostic assay for presence of a microbial infection; optionally repeating the debriding step; and applying a wound dressing with or without an antimicrobial agent according to the diagnostic assay. In some embodiments, the diagnostic assay comprises one or more diagnostic disks in fluid communication with the debridement device, a standalone immunoassay, PCR, or ELISA.

Disclosed herein are fabric materials and kits encompassing the same comprising gel-forming fibres and an anti-biofilm agent. In some embodiments, the gel-forming fibres sequester disrupted biofilm, microorganisms, wound debris, metal ions, or combinations thereof. In yet other embodiments, the gel-forming fibres are woven, non-woven, knitted, or combinations thereof. In still other embodiments, the gel-forming fibres is selected from the group consisting of sodium carboxymethylcellulose, alginate, cellulose, carboxyethylcellulose, cellulose ethyl sulfonate, modified cellulose, pectin, chitosan, modified chitosan, hyaluronic acid, polysaccharide, gum-derived polymer, and any combination thereof. In still other embodiments, the gel-forming fibres comprise sodium carboxymethylcellulose. In yet other embodiments, the gel-forming fibres comprise an absorbency of at least 10 g/g. In some embodiments, the gel-forming fibres comprise an absorbency of 15 g/g to 50 g/g. In still other embodiments, the sodium carboxymethylcellulose has a degree of substitution of at least 0.05 carboxymethyl groups per cellulose unit. In still other embodiments, the sodium carboxymethylcellulose has a degree of substitution of at least 0.2 carboxymethyl groups per cellulose unit. In yet other embodiments, the sodium carboxymethylcellulose has a degree of substitution of between 0.3 and 0.5 carboxymethyl groups per cellulose unit. In yet other embodiments, the anti-biofilm agent is selected from the group consisting of ethylenediaminetetraacetic acid (EDTA), tetrasodium EDTA, disodium EDTA, epigallocatechin gallate (EGCG), ellagic acid, esculetin, fisetin, reserpine, quercetin, linoleic acid, berberine, chitosan, eugenol, curcumin, synthetic halogenated furanone (F-56), Peptide 1018, CFT073 group-II capsular polysaccharide (Serotype K2), Pel polysaccharide, Psl polysaccharide, sophorolipid, colistin, nisin, subtilin, epidermin, gallidermin, sodium citrate, tannic acid, deoxyribonuclease I, glycoside hydrolase, bacteriophage-encoded endolysin (PlyC), silver, octenidine hydrochloride, chlorhexidine, cadexomer iodine, polyhexamethylene biguanide, usnic acid, benzethonium chloride (BC), aryl rhodanines, cis-2-decenoid acid (C2DA), and dispersin B.

Disclosed herein are methods, devices and kits for debridement of a wound, comprising: a) a device for debridement of a wound as described herein; and b) a solution or formulation for enhancing or assisting in debridement of the wound. In some embodiments, the solution or formulation for enhancing or assisting in debridement of the wound comprises antimicrobial agents, anti-biofilm agents, metal chelators, surfactants, or any combination thereof. In some embodiments, anti-biofilm agent is selected from the group consisting of ethylenediaminetetraacetic acid (EDTA), tetrasodium EDTA, disodium EDTA, epigallocatechin gallate (EGCG), ellagic acid, esculetin, fisetin, reserpine, quercetin, linoleic acid, berberine, chitosan, eugenol, curcumin, synthetic halogenated furanone (F-56), Peptide 1018, CFT073 group-II capsular polysaccharide (Serotype K2), Pel polysaccharide, Psl polysaccharide, sophorolipid, colistin, nisin, subtilin, epidermin, gallidermin, sodium citrate, tannic acid, deoxyribonuclease I, glycoside hydrolase, bacteriophage-encoded endolysin (PlyC), silver, octenidine hydrochloride, chlorhexidine, cadexomer iodine, polyhexamethylene biguanide, usnic acid, benzethonium chloride (BC), aryl rhodanines, cis-2-decenoid acid (C2DA), and dispersin B. In some embodiments, the anti-biofilm agent is present between 0.01-5% by weight. In some embodiments, the metal chelator comprises ethylenediaminetetraacetic acid (EDTA). In some embodiments, the EDTA is present at a concentration of at least 0.01% by weight. In some embodiments, the EDTA is present at a concentration between 0.2-0.8% by weight. In some embodiments, the surfactant comprises a cationic surfactant, an anionic surfactant, a zwitterionic surfactant, a non-ionic surfactant, or a combination thereof. In some embodiments, the surfactant is present at less than 2% by weight. In some embodiments, the surfactant is present at 0.01-2% by weight. In yet other embodiments, the solution or formulation comprises sterile water or saline. In yet other embodiments, the solution or formulation comprises an oxidizing agent. In some embodiments, the oxidizing agent is hydrogen peroxide. In yet other embodiments, the solution or formulation comprises iodine, polyhexanide (PHMB), chlorhexidine, hypochlorous acid, sodium hypochlorite, chlorine dioxide, acetic acid, or a combination thereof. Methods, devices, and kits, in some embodiments, further comprise a treating agent. In some embodiments, the treating agent comprises an antimicrobial or anti-biofilm composition. Methods, devices, and kits, in some embodiments, further comprise instructions for use.

Disclosed herein are methods, devices and kits for detecting an infection in a sample, comprising: a) a debridement device as described herein for collecting the sample; b) a diagnostic unit in fluid communication with the debridement device, wherein the diagnostic unit comprises an enzyme-based assay, an electronic sensor, or one or more reagents for indicating the infection; and c) a viewing window or reporter area wherein a color, color change, or other detectable signal based on the enzyme-based assay, the electronic sensor, or the one or more reagents for indicating the infection is observed. In some embodiments, the one or more reagents is selected from the group consisting of enzyme-reactive indicators, enzymes that produce colored products, pH indicators, protein responsive reagents, and moisture-detecting reagents. In some embodiments, the enzyme-reactive indicators interact with one or more enzymes selected from the group consisting of elastase, lysozyme, cathepsin G, and myeloperoxidase. Methods, devices, and kits, in some embodiments, further comprise a wound dressing comprising gel-forming fibres with or without an antimicrobial agent. Methods, devices, and kits, in some embodiments, further comprise instructions for use.

Disclosed herein are methods, devices and kits for debridement of a wound, comprising a wound contacting layer comprising one or more foams. In some embodiments, the one or more foams comprises open pore foams. In some embodiments, a first foam of the one or more foams is on a first side and a second foam of the one or more foams is on a second side. In some embodiments, the first foam comprises a rough texture. In some embodiments, the second foam comprises a smooth texture. In some embodiments, a first foam of the one or more foams and a second foam of the one or more foams are on a same side. In some embodiments, the one or more foams comprises polyurethane. In some embodiments, the one or more foams is in a butterfly shape. In some embodiments, a pore of the one or more open foams comprises at diameter in a range of about 10 um to about 500 um. In some embodiments, a height of the one or more open foams is in a range of about 1 centimeter to about 5 centimeters. In some embodiments, a width of the one or more open foams is in a range of about 1 centimeter to about 10 centimeters. In some embodiments, a length of the one or more open foams is in a range of about 1 centimeter to about 15 centimeters.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 1A-1C illustrate various forms of a debridement device 100 comprising a wound contacting layer 102 with a layer of monofilaments or bristles 104 in contact with a layer of gel-forming fibres 106. Some embodiments have a base layer for support 108. The debridement device 100 can be in the form of a stick or swab, with different shapes for the wound contacting surface, including a rectangular shape (FIG. 1A), a tubular shape (FIG. 1B), and a rounded or spear shape (FIG. 1C). A stick or handle 110 can comprise a hollow tube, a shaft, or a flat stick.

FIGS. 2A-2C illustrate various forms of another embodiment of a debridement device 200, comprising a layer of monofilaments 202 in contact with a layer of gel-forming fibres 204. In some embodiments, the debridement device 200 further comprises a support layer 206 that may be formed of foam, fabric, paper, polymer, plastic, or any other similar material or combination of material. The support layer 206 may be in contact with the fibres 202. In some embodiments, the debridement device 200 comprises fibre blends within or between layers. In FIG. 2A (magnified image), for example, the support layer 206 may comprise a fabric layer and a foam layer on top of a hydrofibre and monofilament layer. In some embodiments, the debridement device 200 is a square or rectangular shape (FIG. 2A), a circular or elliptical shape (FIG. 2B), or a triangular shape (FIG. 2C). In some embodiments, the debridement device 200 is a pad with a plurality of bristles 208 or a pile of monofilaments in contact with a layer of gel-forming fibres 208. In some embodiments, the pad has a backing 210, comprising a fabric or fiber blends. Further still, the backing 210 may have an anti-slip surface. The debridement device 200 may also have a diagnostic unit 212 that is in fluid communication with a wound contacting layer 214.

FIGS. 3A-3F illustrate types of handles 302, 304, 306, 308, 310 in contact with an outer support layer or a non-wound-contacting surface 312 of debridement pads 300. The debridement pads 300 may have a layer of gel-forming fibres with a pile of monofilaments or synthetic fibres on its surface as discussed herein. Different forms of handle include a soft fabric grip handle 302, soft fabric pocket or sleeve handle 308, fins 304 or tabs 310 that can be lifted when in use or folded flat when not in use, a Velcro® or hook-an-loop securing unit that allows one to removably attach a plastic handle or knob 306, or an anti-slip layer 316 comprising silicone.

FIGS. 5A-5D illustrate wicking guide mechanisms 500 that provide a fluid communication between the debridement device and the diagnostic unit, including a hole 502 that allows fluid flow (FIG. 5A), wicking material 504 such as gelling fibres or similar wicking fibres that wick fluid from the debridement device to the diagnostic unit (FIG. 5B), a dimple or concave feature 506 comprising a non-woven material, fabric, or filter paper protruding outward to wick fluid (FIG. 5C), and a hydrophilic or gelling fiber disk 508 (FIG. 5D)

DETAILED DESCRIPTION

Figure 4:
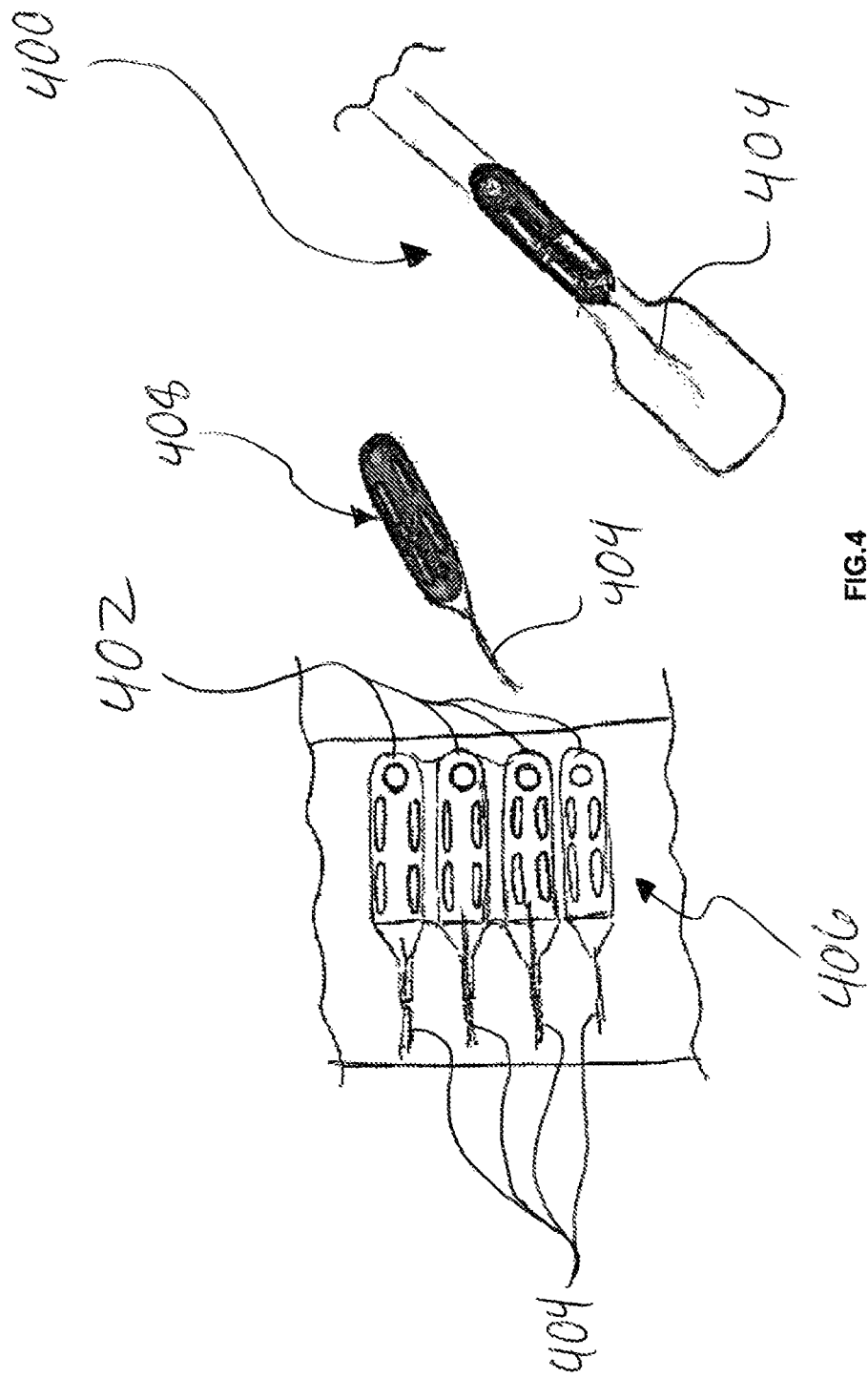
FIG. 4 illustrates a debridement device 400 in fluid communication with a diagnostic unit 402 that detects a wound infection. In one example, the diagnostic unit 402 comprises a diagnostic disk comprising reagents printed or deposited on a solid phase, such as filter paper, and wicking fibres or threads 404, such as gelling fibres, that provide a fluid communication between the debridement device 400 and the diagnostic unit/disk 402. In some embodiments, the debridement device 400 with infection detection comprises either a separate sticker 406 that is placed onto the debridement device 400, or is directly printed onto the debridement device. In some embodiments, the sticker 406 or infection detection design can comprise different patterns. In yet another embodiment, the diagnostic unit 402 may be an electronic sensor 408 capable of detecting infection.

Provided herein are devices and methods for debridement, optionally in combination with diagnosis or testing of wound exudate or surface. In some embodiments, the devices provided herein comprise a wound contacting layer, the wound contacting layer comprising at least one layer, a plurality of layers, or a pile of fibres, filaments or bristles, the wound contact layer optionally in contact with or used in conjunction or in combination with the surface of a layer of hydrophilic fibres or gelling fibres. The layer of gelling fibres may comprise an absorbent material. In some embodiments, the gelling fibres are arranged as one or more layers. In some embodiments, the fibres, filaments or bristles protrude from a layer of gelling fibres or are perpendicular to the layer of gelling fibres. In some embodiments, the bristles comprise a pile of nylon monofilaments that can loosen or remove unwanted tissue on a wound without causing significant trauma to the wound site. The bristles may also comprise other synthetic fibres with textured surfaces to allow efficient debridement. In some embodiments, the devices and methods for debridement disclosed herein are capable of absorbing and sequestering wound exudate, metal ions, or bacteria. In some embodiments, the devices and methods for debridement disclosed herein are capable of selectively and atraumatically removing unwanted tissues from infected sites. In some embodiments, the devices and methods for debridement disclosed herein are capable of disrupting and sequestering microbial biofilm. In some embodiments, the devices and methods for debridement disclosed herein are in fluid communication with a diagnostic unit for in situ detection of a microbial infection. In some embodiments, a sample of wound tissue can be obtained from the devices for debridement disclosed herein, and analyzed for the presence of a microbial infection using, for example, any standard diagnostic assay, including PCR, enzyme-linked immunosorbent assay (ELISA), and other immunoassays.

Definitions

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

"About" as used herein when referring to a measurable value such as an amount, a temporal duration, and the like, is meant to encompass variations of ±20% or ±10%, or ±5%, or even ±1% from the specified value, as such variations are appropriate for the disclosed values or to perform the disclosed methods.

Unless defined otherwise, all technical and scientific terms used herein have the same meaning as is commonly understood by one of skill in the art to which this disclosure belongs.

As used herein, the term "filament" may refer to a "monofilament." In some embodiments, the term "monofilament" refers to a single strand of thread or yarn. The thread or yarn can be a synthetic material. Monofilaments may form bristles. Non-limiting examples of synthetic materials that form monofilaments or bristles include nylon, polyester, polypropylene, polygalactic acid, acrylic, acetal, polyvinyl chloride (PVC), polycarbonate, silicone, chemically modified fibres, or any combination thereof. In some embodiments, monofilaments comprise textured surfaces, such as micro-hooks or barbs that help to debride a wound surface, i.e., loosen or remove unwanted tissue. In some cases, monofilaments may also be referred to as bristles or debridement fibres.

As used herein, the terms "hydrophilic fibres" or "hydrofibres" or "gel-forming fiber" refer to fibres that have high absorption capability and resist lateral spread or diffusion of a liquid upon absorption. In some embodiments, hydrophilic fibres form a gel upon contact with a fluid to sequester or lock in the fluid, thus resisting lateral spread of the fluid. One example of gel-forming fibres is AQUACEL®. In some embodiments, gelling fibres can sequester unwanted wound materials, such as loosened biofilm, wound debris, metal ions, and bacteria, thus preventing or mitigating further infection and helps to keep a wound clean and dry. For examples, gel-forming fibres have an absorbency of at least 10 g/g or 15 g/g to 50 g/g and resists lateral spread of a fluid upon absorption may be used.

In some embodiments, gelling fibres comprise carboxymethylcellulose with varying degree of substitution, e.g., at least 0.05, at least 0.2, or between 0.3 and 0.5 carboxymethyl groups per cellulose unit. In some embodiments, gelling fibres comprise a surfactant, metal chelator, or antimicrobial agent. In other embodiments, gel-forming fibres are selected from the group consisting of sodium carboxymethylcellulose, alginate or derivatized alginate, cellulose, carboxyethylcellulose, cellulose ethyl sulfonate, modified cellulose or derivatized cellulose, pectin, chitosan, modified chitosan or derivatized chitosan, hyaluronic acid or derivatives, polysaccharide, gum-derived polymer, polyacrylic acid or derivatives, and any combination thereof.

As used herein, "degree of substitution" refers to the average number of carboxymethylated hydroxyl groups per glucose or cellulose unit present in a cellulosic polymer such as carboxymethylcellulose. Degrees of substitution of carboxymethylcellulose can range from about 0.05 to about 0.5 carboxymethyl groups per cellulose unit, about 0.2 to about 0.5 carboxymethyl groups per cellulose unit, about 0.3 to about 0.5 carboxymethyl groups per cellulose unit. Degree of substitution can be about 0.05, about 0.06, about 0.07, about 0.08, about 0.09, about 0.1, about 0.2, about 0.3, about 0.4, about 0.5, about 0.6, about 0.7, about 0.8, about 0.9, or about 1.0 carboxymethyl groups per cellulose unit.

As used herein, the term "swab tip" or "swabbing end" refers to the wound-contacting end of a debridement device that can comprise one or more support layers, fibres or a fiber blend, or monofilaments. The terms swab tip and swabbing end are used interchangeably.

As used herein, the term "sensor unit" or "diagnostic unit" refers to a separate unit or chamber that comprises reagents for the detection of an infection. The terms sensor unit, diagnostic unit, and sensor chamber are used interchangeably herein.

In some embodiments, the devices and methods for debridement disclosed herein may comprise other materials that absorb wound exudate, including fabric materials. Such fabric materials are broadly known, and may include foams, superabsorbent fibres, gelling foams, directional foams and the like.

According to certain embodiments, the herein described devices for wound debridement and disruption of microbial biofilm comprise a layer monofilaments or bristles that loosen or remove unwanted or necrotic tissue on a wound surface and a layer of high-absorbency gel-forming fibres, such as AQUACEL®, or similar hydrophilic fibres, that can sequester wound fluid, bacteria, metal ions, and other unwanted tissue. In some embodiments, the gelling fibres or hydrophilic fibres form an absorbent layer. The gelling fibres suitable for use in the absorbent layer of the present disclosure include hydrophilic fibres, which upon contact with a fluid or wound exudate, form a gel and sequester moisture and absorbed materials, such as disrupted biofilm, bacteria, or unwanted wound tissue, for examples.

Further described herein are fabric materials capable of disrupting biofilm and/or adsorbing disrupted biofilm. In some embodiments, the fabric materials comprise anti-biofilm activity. In some embodiments, the fabric materials sequester wound fluid, bacteria, metal ions, or other wound debris. In some embodiments, the fabric materials comprise anti-biofilm activity and sequester wound fluid, bacteria, metal ions, or other wound debris. In some embodiments, the fabric materials improve susceptibility of microorganisms to antimicrobial agents. In some instances, the fabric materials as described herein reduce microbial burden at a colonized or infected site. In some instances, the fabric materials reduce microbial burden at a colonized or infected site without antimicrobial agents. In some instances, the fabric materials reduce microbial burden at a colonized or infected site with a low amount of antimicrobial agents.

The fabric materials as described herein, in some embodiments, comprise various structures. Such structures include nonwoven fabrics, woven fabrics, composites, laminates, foams, knitted fabrics and combinations thereof. In some embodiments, the fabric materials comprise gelling fibres or hydrophilic fibres.

In some embodiments, the gelling fibres disrupt the biofilm by removing moisture from the biofilm. In some embodiments, the gelling fibres remove moisture by forming an absorbent layer. In some embodiments, the gelling fibres form a gel on contact with the moisture.

In some embodiments, the gelling fibres comprises gel-forming polymers or gelling fibres that have high absorbency and resist lateral spread upon absorption of a fluid. In some embodiments, the gelling fibres absorb and retain disrupted biofilm, microorganisms, and/or other wound debris. In some embodiments, the gelling fibres are configured to sequester metal ions. In some embodiments, the gelling fibres form a layer. Non-limiting examples of gel-forming polymers include cellulose, carboxymethylcellulose (CMC), carboxyethylcellulose, AQUACEL®, oxidized cellulose (or a derivative thereof), cellulose ethyl sulfonate, other chemically modified cellulose, pectin, alginate, chitosan, modified chitosan, hyaluronic acid, polysaccharide, gum-derived polymer, or any combination thereof. In some embodiments, the fibres comprise polyvinylpyrrolidone, polyvinyl alcohols, polyvinyl ethers, polyurethanes, polyacrlyates, polyacrylamides, collagen, gelatin or mixtures thereof. In some embodiments, the gelling fibres comprise a blend of carboxymethylcellulose and alginate. In some embodiments, the gelling fibres comprise a nonwoven layer of gel-forming fibres.

In other embodiments, the gel-forming fibres are selected from the group consisting of sodium carboxymethylcellulose, alginate, cellulose, carboxyethylcellulose, cellulose ethyl sulfonate, modified cellulose, pectin, chitosan, modified chitosan, hyaluronic acid, polysaccharide, gum-derived polymer, and any combination thereof.

In some embodiments, the cellulosic gelling fibres may have a degree of substitution of at least 0.05 carboxymethyl groups per cellulose unit. In some embodiments, the degree of substitution of the carboxymethylcellulose gel-forming fibres is at least 0.2 carboxymethyl groups per cellulose unit, more particularly between 0.3 and 0.5. In some embodiments, the gelling fibres comprise sodium carboxymethylcellulose with a comparatively lower degree of substitution.

The ability to absorb moisture, gel, and disrupt materials such as biofilm is related to the degree of substitution of the cellulosic gelling fiber, including carboxymethylcellulose, as well as to the type of gelling fiber. In some embodiments, the gelling fibres comprise a blend of carboxymethylcellulose with different degrees of substitution, thereby providing for different rates of disruption, absorption, and gelling. In some embodiments, the gelling fibres comprise a blend of different fiber types to provide for disruption and absorption at the same time. In some embodiments, the gel-forming action of the fibres helps to sequester or lock in unwanted wound materials, such as exudate, bacteria, or biofilm, which helps to keep a wound clean and dry, and mitigates or prevents the spread of an infection.

In some embodiments, the fabric material described herein comprises an agent comprising anti-biofilm activity. In some embodiments, the agent comprising anti-biofilm activity comprises no antimicrobial activity. In some embodiments, the agent comprising anti-biofilm activity comprises low levels of antimicrobial activity. Exemplary agents comprising antimicrobial activity include, but are not limited to, silver, antibiotics, antiseptics, antivirals, or antifungals.

In some embodiments, the fabric material comprises one or more agents comprising anti-biofilm activity. In some embodiments, the agent comprising anti-biofilm activity is isolated from natural sources or is a synthetic compound, a chelating agent, a lantibiotic, a small molecule, an ion, a peptide, an enzyme, or a nanoparticle. Exemplary agents comprising anti-biofilm activity include, but are not limited to, ethylenediaminetetraacetic acid (EDTA), tetrasodium EDTA, disodium EDTA, epigallocatechin gallate (EGCG), ellagic acid, esculetin, fisetin, reserpine, quercetin, linoleic acid, berberine, chitosan, eugenol, curcumin, synthetic halogenated furanone (F-56), Peptide 1018, CFT073 group-II capsular polysaccharide (Serotype K2), Pel polysaccharide, Psl polysaccharide, sophorolipid, colistin, nisin, subtilin, epidermin, gallidermin, sodium citrate, tannic acid, deoxyribonuclease I, glycoside hydrolase, bacteriophage-encoded endolysin (PlyC), silver, octenidine hydrochloride, chlorhexidine, cadexomer iodine, polyhexamethylene biguanide, usnic acid, benzethonium chloride (BC), aryl rhodanines, cis-2-decenoid acid (C2DA), and dispersin B.

The fabric material comprising anti-biofilm activity, in some embodiments, further comprises low levels of antimicrobial activity. In some embodiments, the fabric material comprising anti-biofilm activity further comprises no antimicrobial activity.

Described herein are fabric materials comprising agents capable of sequestering biofilm components. In some embodiments, the agents capable of sequestering biofilm components include, but are not limited to, ethylenediaminetetraacetic acid (EDTA), alkali metal salts, alkaline earth metal salts, ammonium salts thereof, and tetraalkylammonium salts.

Fabric materials as described herein may improve the susceptibility of microorganisms to antimicrobial agents. In some instances, the fabric materials improve the susceptibility of microorganisms to antimicrobial agents by disrupting of biofilm and/or sequestering biofilm structural components, metal ions, wound exudate, microorganisms, and/or other wound debris. In some instances, the fabric materials comprise an agent that provides anti-biofilm activity and low antimicrobial activity. Antimicrobial activity may be provided by an antimicrobial agent including, but are not limited to, silver, antibiotics, antiseptics, antivirals, or antifungals. In some instances, following disruption of the biofilm and/or sequestration, the fabric materials further provides antimicrobial effects.

Fabric materials as described herein comprising anti-biofilm activity and/or sequestration ability, in some embodiments, improve efficacy of biofilm disruption over, for example, standard debridement methods, including use of saline and gauze. In some instances, the improved efficacy of biofilm disruption is at least 10%, 15%, 20%, 25%, 30%, 35%, 40%, 45%, 50%, 55%, 60%, 65%, 70%, 75%, 80%, 90%, 95%, 99%, or more than 99%. In some embodiments, fabric materials improve susceptibility of microorganisms to antibacterial agents. In some instances, the improved susceptibility of microorganisms to antibacterial agents is at least 10%, 15%, 20%, 25%, 30%, 35%, 40%, 45%, 50%, 55%, 60%, 65%, 70%, 75%, 80%, 90%, 95%, 99%, or more than 99%.

In some instances, the fabric materials as described herein reduce microbial burden at a colonized or infected site by at least 10%, 15%, 20%, 25%, 30%, 35%, 40%, 45%, 50%, 55%, 60%, 65%, 70%, 75%, 80%, 90%, 95%, 99%, or more than 99%. In some instances, the fabric materials reduce microbial burden at a colonized or infected site in a range of about 10% to about 99%, about 20% to about 80%, about 30% to about 70%, or about 40% to about 60%.

Debridement Fibres

In some embodiments, the bristles, monofilaments, or debridement fibres are textured fibres or filaments that withstand the debriding action and help to loosen or remove unwanted tissue on a wound. In some embodiments, bristles or monofilaments comprise nylon, acetal, polypropylene, acrylic, polyvinyl chloride (PVC), polycarbonate, silicone, wool, or any combination thereof.

In some embodiments, the debridement fibres are woven or nonwoven. In some embodiments, the nonwoven fibres form a layer. In some embodiments, the fibres are woven into a perpendicular or bristle-type arrangement. In some embodiments, the perpendicular or bristle-like arrangement comprises monofilaments.

In some embodiments, the debridement fibres are on the surface of or are in contact with the layer of gelling fibres to provide a disruptive or loosening effect followed by an absorptive effect by the gelling fibres. Thus, contacting a wound or biofilm with the debridement fibres may result in physically breaking up wound debris or biofilm, allowing for absorption of the material. In some embodiments, the gelling action of certain fibres, such as AQUACEL®, further provides for sequestration of the absorbed materials. Such sequestration helps to clean a wound efficiently before applying a wound dressing, comprising gelling fibres.

In some embodiments, the debridement device includes anti-biofilm agents such as metal chelators or surfactants. In some embodiments, the debridement fibres loosen unwanted tissues and materials through the action of surfactants and anti-biofilm components. In some embodiments, the debridement device, which has high absorbency and sequesters wound particulates, provides an easy and fast means for diagnosis or detection of a microbial infection in a wound. In such embodiments, the debridement device is in fluid communication with a diagnostic unit, such as a diagnostic disk comprising one or more reagents printed on or deposited on a filter paper, for in situ diagnosis. Fluid communication in such embodiment comprises gelling fibres or hydrophilic threads, an opening, or filter paper that help to wick wound fluid or material from the layer of gelling fibres to the reagents in the diagnostic disk. In some embodiments, the diagnostic disk is embedded in or inserted into a debridement device to allow facile detection of a bacterial infection in situ. In some embodiments, such diagnostic disk is used in a standalone diagnostic device, wherein a sample of a wound can be extracted from the debridement device for further analysis using one or more conventional diagnostic assays, such as PCR, ELISA, or immunoassay.

Debridement Devices

In some embodiments, the debridement devices disclosed herein comprise debridement sticks or stick-swab devices. In some embodiments, the debridement devices disclosed herein comprise debridement swabs. In some embodiments, the debridement devices comprise debridement pads or pads with a backing, optionally with a handle. In some embodiments, the debridement devices disclosed herein comprise gel-forming fibres and a layer of bristles or monofilaments. In some embodiments, the gel-forming fibres comprise carboxymethylcellulose, such as AQUACEL®.

In some embodiments, the debridement devices comprise a pile of monofilaments or bristles that protrude from the gel-forming fibres or are perpendicular to and in contact with the layer of gel-forming fibres. In some embodiments, the monofilaments or bristles comprise nylon fibres. Other materials that can be used for monofilaments or bristles for debriding a wound include, but are not limited to, acetal, polypropylene, acrylic, polyvinyl chloride (PVC), polycarbonate, silicone, wool, or any combination thereof.

In some embodiments, the layer of gel-forming fibres is arranged in a layered structure that comprises support materials. Support materials can form a base layer that is in contact with the layer of gel-forming fibres. Support materials include foam, fabric, paper, plastic, wood, polymer, or any combination thereof, for example. The layered structure may further comprise an outer layer that covers the base layer or an outer transparent layer to allow visual detection of a diagnostic insert embedded or inserted in a debridement device for in situ detection of a microbial infection. For example, fabric as an outer layer may cover a foam layer, with the foam layer located between the gel-forming fiber layer and the outer fabric layer. In some embodiments, the outermost layer comprises an anti-slip material for holding the debridement device, such as silicone.

Debridement devices as described herein, in some embodiments, comprise one or more foams. In some embodiments, the one or more foams comprises open pore foams. In some embodiments, the one or more foams are the same type of foam. In some embodiments, the one or more foams are different types of foam. In some embodiments, the one or more foams comprise variable abrasiveness. For example, a first foam on a first side comprises a rough texture and a second foam of a second side comprises a smooth texture. In some embodiments, the first foam and the second foam are on a same side. In some embodiments, the first foam comprising a rough texture is used for debridement. In some embodiments, the second foam comprising a smooth texture is used for absorbance.

In some embodiments, the one or more foams are porous. In some embodiments, the one or more foams comprise different pore sizes. In some embodiments, a first foam on a first side comprises a first pore size. In some embodiments, a second foam on a second side comprises a second pore size. In some embodiments, the first foam on the first side and the second foam on the second side comprise the same pore size. In some embodiments, the first foam and the second foam are on the same side and comprise the same pore size. In some embodiments, a pore of the one or more foams comprises a diameter of at least or about 10, 20, 30, 40, 50, 60, 70, 80, 90, 100, 120, 140, 160, 180, 200, 220, 240, 260, 280, 300, 320, 340, 360, 380, 400, 500, 600, 700, 800, 900, 1000, or more than 1000 micrometers (um). In some embodiments, a pore of the one or more foams comprises a diameter in a range of about 10 um to about 1000 um, about 20 um to about 800 um, about 30 to about 700 um, about 40 to about 600 um, about 50 to about 500 um, about 60 um to about 400 um, about 70 um to about 300 um, about 80 um to about 200 um, or about 90 um to about 150 um.

In some embodiments, the one or more foams comprise various materials. In some embodiments, the one or more foams comprises polyurethane, polyethylene, a silicone resin, a natural and synthetic rubber, polyglycolic acid, polylactic acid, or a copolymer thereof a synthetic polymer, such as polyvinyl alcohol and polyvinylpyrolidone; a natural polymer, such as collagen, gelatin, karaya gum, guar gum, hyaluronic acid, sodium alginate, chitin, chitosan, fibrin, and cellulose, or a synthetic polymer derived therefrom; and a mixture thereof. In some embodiments, the one or more foams polyurethane.

In some embodiments, a first foam on a first side comprises a first material. In some embodiments, a second foam on a second side comprises a second material. In some embodiments, a the first foam and the second foam are on a same side. In some embodiments, the first material and the second material are the same. In some embodiments, the first material and the second material are different. In some embodiments, the first material comprises polyurethane, polyethylene, a silicone resin, a natural and synthetic rubber, polyglycolic acid, polylactic acid, or a copolymer thereof; a synthetic polymer, such as polyvinyl alcohol and polyvinylpyrolidone; a natural polymer, such as collagen, gelatin, karaya gum, guar gum, hyaluronic acid, sodium alginate, chitin, chitosan, fibrin, and cellulose, or a synthetic polymer derived therefrom; and a mixture thereof. In some embodiments, the second material comprises polyurethane, polyethylene, a silicone resin, a natural and synthetic rubber, polyglycolic acid, polylactic acid, or a copolymer thereof; a synthetic polymer, such as polyvinyl alcohol and polyvinylpyrolidone; a natural polymer, such as collagen, gelatin, karaya gum, guar gum, hyaluronic acid, sodium alginate, chitin, chitosan, fibrin, and cellulose, or a synthetic polymer derived therefrom; and a mixture thereof.

In some embodiments, the debridement devices comprise one or more foams, wherein the one or more foams are of various shapes. In some embodiments, the one or more foams are a butterfly shape. In some embodiments, the one or more foams are a rectangular shape. In some embodiments, the one or more foams are a circular shape. In some embodiments, the one or more foams are a cylindrical shape.

In some embodiments, the debridement device comprises one or more foams of varying sizes. In some embodiments, a length of the one or more foams is at least or about 1.0, 1.5, 2.5, 3.0, 3.5, 4.0, 4.5, 5.0, 5.5, 6.0, 6.5, 7.0, 7.5, 8.0, 8.5, 9.0, 9.5, 10.0, or more than 10 centimeters (cm). In some embodiments a width of the one or more foams is at least or about 1.0, 1.5, 2.5, 3.0, 3.5, 4.0, 4.5, 5.0, 5.5, 6.0, 6.5, 7.0, 7.5, 8.0, 8.5, 9.0, 9.5, 10.0, or more than 10 centimeters (cm). In some embodiments, a height of the one or more foams is at least or about 1.0, 1.5, 2.5, 3.0, 3.5, 4.0, 4.5, 5.0, 5.5, 6.0, 6.5, 7.0, 7.5, 8.0, 8.5, 9.0, 9.5, 10.0, or more than 10 centimeters (cm). In some embodiments, a length, width, or height is in a range of about 1 centimeter to about 15 centimeters, about 2 centimeters to about 12 centimeters, about 3 centimeters to about 10 centimeters, or about 4 to about 8 centimeters.

In some embodiments, the debridement devices disclosed herein further comprise a mechanism that allows for detection of infection of a wound. An exemplary mechanism that allows for detection of infection of a wound comprises a diagnostic unit. The diagnostic unit may be attached to the debridement device. Attachment may be in the form of an adhesive or any other suitable means that allows the diagnostic unit to be in fluid communication with the layer of gel-forming fibres in the debridement device. As an example, one or more diagnostic disks, comprising reagents deposited or printed on filter paper or similar support phase, may be attached to a debridement device, such as the handle of a stick-swab debridement device, with fluid communication between the diagnostic disk and the layer of gel-forming fibres formed by a wicking mechanism, such as wicking threads, filter paper, or a conduit for fluid flow. Additional mechanisms that allow for detection of infection with the combined use of a debridement device include embedding reagents or a diagnostic disk containing such reagents in a layer of gel-forming fibres with a transparent cover that allows visualization of the diagnostic disk, for example.

A diagnostic disk can comprise a reaction layer comprising one or more reagents that interact with a target enzyme indicative of a microbial infection, wherein the reagents are affixed to a solid phase; each reagent is sprayed, printed, or deposited in a reagent area separated by impermeable separators; each reagent area comprises a reporter area wherein a color, color change, or other detectable signal is observed; and a transparent cover comprising a window for visualizing the signal in the reporter area.

In still further embodiments, a wound sample can be extracted from the debridement device, which can be analyzed separately by any suitable diagnostic assay.

In some embodiments, the wound contacting layer further comprises a wicking guide mechanism, including, for example, one or more wicking stitching or wicking tufting or wicking threads, comprising gelling fibres or hydrophilic threads. The wicking guide mechanism provides fluid communication between reagents, such as reagents in a reagent layer of a diagnostic disk, for example, and the debridement device, such as the layer of gel-forming fibres. The wicking action allows fluid and unwanted materials, such as disrupted biofilm, bacteria, and wound debris, to be directed from the debridement device to a diagnostic disk or a reaction area where reagents are deposited for analyzing a wound sample for the presence of a microbial infection. Thus, the wicking guide mechanism provides a means for fluid communication between the debridement device and a diagnostic unit, either attached to the debridement device externally or embedded in a debridement device or a debridement pad in the form of a diagnostic disk. Wicking fibres that are wettable and exhibit capillary action may be used for wicking stitching or wicking tufting or as fiber threads to form fluid communication between the wound material sequestered by the debridement device and the diagnostic reagents. In some embodiments, the wicking fibres are solid or hollow. Examples of wicking fibres include, but are not limited to, cotton, rayon, viscose, wool, silk, polyester, polyamide, CMC, and polypropylene.

Reagents And Assays

Any assay for the detection of an analyte associated with an infection can be used. Analytes associated with infection include structural components of an infectious organism such as a bacterium, fungus, protist, or a virus, for example. Analytes associated with infection also include biomarkers that are upregulated in response to infection. Such biomarkers may be associated with a host immune response to the infection. Exemplary biomarkers include lysozyme, MPO, cathepsin G, elastase, catalase, lipase, or esterase.

Assays for the detection of infection include immunoassays, such as enzyme-linked immunosorbent assay (ELISA), Western Blotting, or any other immunoassay that allows for the detection of an analyte associated with an infection. Additional assays for the detection of infection include polymerase chain reaction (PCR). These assays may be used to directly test for the presence of an infectious organism, such as a bacterium, fungus, protist, or a virus. For example, PCR may be used to test for the presence of DNA and RNA such as transcripts or structural RNA molecules of an infectious organism. These assays may also be used to determine upregulation of a biomarker in response to infection. Examples of biomarkers upregulated in response to infection include proteins, cytokines, and chemokines associated with a host immune response to infection.

Assays further include reactions or processes that produce a visible color change or other detectable signal under conditions associated with the presence of infection. Suitable reagents include enzyme-reactive indicators, reagents that are sources of peroxide, enzymes that produce colored products, pH indicators, protein responsive reagents, and moisture-detecting reagents, for example. Moieties of enzyme-reactive indicators that are capable of producing a color change or detectable signal include, for example, a peroxidase substrate, arylamine, an amino phenol, a neutral dye, a charged dye, a nanoparticle, a colloidal gold particle, or an analog thereof. Examples of pH-sensitive reagents capable of producing a color change or detectable signal include bromothymol blue, phenol red, bromophenol red, chlorophenol red, thymol blue, bromocresol green, bromocresol purple, nitrazine yellow, or other sulfonephthalein dyes.

Kits And Instructions

Provided herein are containers and kits that can be used in combination with the herein described devices for debridement and microbial/infection detection. The present disclosure further provides instructions that can direct a user (e.g., a human user) to use the devices and methods disclosed herein, as well as the containers and kits that comprise such debridement and microbial/infection detection devices and methods disclosed herein.

Containers for use with the methods and devices disclosed herein can be used to store, transport, and/or aliquot the devices and solutions useful for debridement and/or diagnosing and detecting a microbial infection. In some embodiments, the containers provided herein may also include cleansing agents, therapeutic agent(s), such as antimicrobial and/or anti-biofilm compositions, and combinations thereof, for treatment of detected infections. Such containers can, for example, provide conditions suitable for transport and/or storage (e.g., ambient or cooled storage for solution or therapeutic agent transport). In yet other embodiments, the containers provided herein may contain compartments to divide or segregate parts or solutions of the methods and devices disclosed herein.

Kits of the present disclosure provide various components for using the debridement and microbial/infection detection methods and devices described herein. Such components can include containers, storage equipment, debridement devices, swab or other collection devices, analyzer, control samples, and/or solutions or compositions for cleaning or detecting a microbial infection. Generally, kits allow for user-friendly, accurate and reliable use of the debridement and infection detection devices and methods described herein, including, but not limited to testing, administration, storage, transport, and other components needed to perform the methods and devices for debridement and microbial/infection detection disclosed herein.

In some embodiments, the kits disclosed herein include solutions or formulations that assist in debridement of a wound by lubricating the debridement device prior to wound treatment. The solutions or formulations are physiologically-compatible and may be applied to the debridement device on an as-needed basis. In some instances, the solution or formulations may be physiological saline or other solution compatible with skin and wound surfaces.

The kits disclosed herein may also include solutions or formulations that enhance debridement of a wound. In some embodiments, the solutions or formulations may contain agents that enhance or assist in debridement of a wound. In other embodiments, the debridement devices may include agents that enhance or assist in debridement of a wound. In both instances, a liquid formulation, such as sterile water or saline, is added to assist and/or activate the agents that enhance debridement of a wound.

In some embodiments, the solutions or formulations assist in breaking down biofilm and/or preventing its re-formation in or around the wound. In some embodiments, the solutions or formulations disclosed herein include a metal chelating agent, including but not limited to ethylenediaminetetraacetic acid (EDTA), present as the di-, tri- or tetra-basic salt of EDTA. In some embodiments, the EDTA is present at concentration of at least 0.01%, at least 0.025%, at least 0.05%, at least 0.1%, at least 0.25%, at least 0.5%, at least 1%, at least 2%, at least 4% or at least 5% by weight. In other embodiments, the EDTA is present at levels of between 0.01-4%, between 0.1-4%, between 0.1-3%, between 0.2-3%, between 0.2-2%, between 0.2-1%, or between 0.2-0.8% by weight.

In some embodiments, the solutions or formulation comprise a surface acting agent, including but not limited to cationic surfactants, anionic surfactants, zwitterionic surfactants and non-ionic surfactants compatible with and safe for use with a wound and skin surface. Examples include, but are not limited to, cationic surfactants, including quaternary ammonium salts, alkyl pyridinium salt, alkyl imidazolium salt, alkyl morpholinium salt, a benzethonium salt or an ethoxylated quaternary ammonium salt or mixtures thereof. In some instances, the quaternary ammonium salt may include monoalkyl trimethyl ammonium salt, dialkyl dimethyl ammonium salts, and monoalkyl monobenzyl dimethyl ammonium salts. In some instances the cationic surfactant may include a quaternary cationic surfactant, including a quaternary ammonium surfactant. In some instances the cationic surfactant is chosen from the group consisting of benzethonium, benzalkonium, dimethyldialkylonium, alkylpyridinium and alkyltrimethylammonium cations with any counter ion, for example, bromide, chloride, acetate or methyl sulfate. In some embodiments, the surfactant is present at levels of at least 0.01%, at least 0.025%, at least 0.5%, at least 1%, at least 2% or at least 4% by weight. In some embodiments, the surfactant is present at levels of less than 2%, less than 1%, less than 0.5%, less than 0.25%, less than 0.1%, less than 0.05% and less than 0.025% by weight. In other embodiments, the surfactant is present at levels of between 0.01-2%, between 0.05-2%, between 0.05-1%, between 0.075-1%, between 0.01-1%, or between 0.2-1% by weight.

In some embodiments, the solutions or formulations comprise an antimicrobial and/or anti-biofilm agent. In some embodiments, the antimicrobial and/or anti-biofilm agent is an oxidizing agent, such as peroxides, including hydrogen peroxide, and halogens, such as chlorine, fluorine or iodine, and combinations thereof, that are compatible with and safe for use with a wound and skin surface. In some instances, the antimicrobial and/or anti-biofilm agent is iodine (for example, povidone iodine, cadexomer iodine), polyhexanide (PHMB), chlorhexidine, hypochlorous acid, sodium hypochlorite, chlorine dioxide, acetic acid, and the like and combinations thereof. In some embodiments, the antimicrobial and/or anti-biofilm agent is present at levels of about at least 0.01%, at least 0.05%, at least 0.1%, at least 0.25%, at least 0.5%, at least 1%, at least 2% or at least 5% by weight. In other embodiments, the antimicrobial and/or anti-biofilm agent is present at levels of about between 0.01-5%, between 0.05-4%, between 0.05-3%, between 0.05-2%, between 0.075-1%, between 0.01-1%, or between 0.5-2% by weight.

In yet other embodiments, the antimicrobial and/or anti-biofilm agent is a metal ion, for example, silver, iron, nickel, copper, chromium, manganese, gold, gallium, magnesium, zinc, bismuth, tin and palladium, and combinations thereof, which are compatible with and safe for use with a wound and skin surface. In some embodiments, the metal ion(s) is present at levels of about at least 0.00001%, at least 0.005%, at least 0.01%, at least 0.025%, at least 0.1%, at least 0.5%, at least 1%, at least 2% or at least 5% by weight. In other embodiments, the antimicrobial and/or anti-biofilm agent is present at levels of about between 0.00001-5%, between 0.0001-4%, between 0.001-4%, between 0.05-4%, between 0.1-4%, between 0.5-2%, or between 0.1-1% by weight.

In some embodiments, the kits may include an after-care agent, including agents that assist in periwound skin recovery, including barrier creams and/or ointments, emollients, moisturizers, anti-inflammatory agents, steroids, skin sealants or agents, and combinations thereof, and/or dressings and/or adhesive tape that maintain a moisture balance of the periwound periphery and avoid maceration and further damage to this area.

In some embodiments, buffering agents are included to maintain the pH of the composition about between 4 and 8, between 4 and 6 or between 4.5 and 5.5. The desired pH may be achieved by incorporating buffering agents in the composition. Examples of buffering agents which may be included are citric acid/di-sodium hydrogen phosphate, citric acid/sodium citrate, acetic acid/sodium acetate. The buffering agent may conveniently be present in an amount of about 0.5% to 2% by weight of the composition so as to provide an isotonic composition.

In some embodiments, the kit may contain two or more parts or containers for performing the methods disclosed herein. In some embodiments, the kit may be a two-part system to be used sequentially, for example, a first part comprising a cleansing/loosening step comprising cleansing/loosening solutions, followed by a treatment step comprising, for example, an antimicrobial or anti-biofilm composition. In other embodiments, the first part or second part may also comprise a physical debridement step. In still other instances, the first and second parts of the kits disclosed herein could also comprise debridement tools to assist in physical debridement using the methods and compositions disclosed herein. In yet other instances, the debridement tools may comprise two types of cleansing pads that differ in roughness of the pads: a rougher side of the pad towards cleansing of the wound area, and a smoother pad to allow effective application of the antimicrobial and/or anti-biofilm agent to the cleansed wound tissue.

The present disclosure provides instructions for using kits and/or containers in combination with the methods and devices described herein. The instructions may be on "printed matter," e.g., on paper or cardboard within or affixed to the kit, or on a label affixed to the kit or packaging material, or attached to a vial or tube containing a component of the kit. Instructions may additionally be included on a computer readable medium. Such instructions can direct a user to use the debridement and/or infection detection devices as well as the containers and kits that comprise such methods and devices.

The following Examples are presented by way of illustration and not limitation.

EXAMPLE 1

Stick-Type Debridement Devices

This example describes devices for debridement in the form of a stick with a debridement device at one end of the stick.

Debridement devices 100 that take the form of a stick 110 with a debridement tip 112 are shown in FIGS. 1A-C.

Stick type of debridement devices 100 can take a variety of forms. For example, the debridement device on one end can be rectangular (FIG. 1A), cylindrical, oval, tubular (FIG. 1B), or round (FIG. 1C). A stick-type of debridement device 100 with a round end can take the form of a spear, as shown in FIG. 1C. The debridement device at one end of the stick 110 can be attached to a handle that is a hollow tube, a shaft, a flat bar, or a stick.

The debridement device on one end of the stick 110 comprises a layered structure that comprises a base layer for support (i.e. support layer 108), an absorbent layer of gel-forming fibres 106 in contact with a layer or a pile of monofilaments in the form of a plurality of bristles 104. The absorbent or gel-forming fibres 106 can be hydrophilic fibres, CMC, or AQUACEL®. The layered structure for a rectangular debridement end is shown in FIG. 1A comprises a base or support layer 108 surrounded by gelling fibres from which a pile of monofilaments protrude. Exemplary cross-sectional views of the layered structure of rectangular and cylindrical, oval, or tubular debridement devices in stick format are shown in FIG. 1A and FIG. 1B, respectively.

EXAMPLE 2

Debridement Pads

This example describes debridement devices in the form of debridement pads 200.

Debridement pads 200 are shown in FIGS. 2A-2C. In some embodiments, the debridement pad 200 may be square or rectangular (FIG. 2A), circular or elliptical (FIG. 2B), or triangular (FIG. 2C) in shape. The shape of the debridement pad/device 200 is not important and can be adapted for various types of wounds of different sizes. The important features of a debridement device 200 comprise bristles or brush-like features 208 and gel-forming absorbent material, such as gel-forming fibres 204. The bristles or brush-like features 208 provide debriding function that helps to loosen or remove wound biofilm, unwanted material, or wound debris. Once such wound materials are loosened or removed by the bristles or brush-like features 208, gel-forming absorbent material 204 in contact with the bristles or brush 208 can absorb or sequester such wound materials to clean, treat, or prepare a wound for wound dressing or further treatment. As shown in the inset of FIG. 2A, the pad 200 may form a layered structure comprising a support fabric or backing 210, a support layer 206 that may be foam for further support, and an absorbent fiber layer comprising gel-forming fiber 204 with a layer or a pile of monofilaments or synthetic fibres on a wound contacting layer 214. Alternatively, the layered structure may comprise a blend of different fibres. The outer layer can comprise monofilaments that form the wound contacting layer 214.

EXAMPLE 3

Debridement Pad Handles and Support Layers

This example describes debridement pad handles and support layers.

Various embodiments of debridement pad handles 302, 304, 306, 308, 310 and support layer structures along the non-wound contacting surface 312 are shown in FIGS. 3A-3F.

A handle may be directly attached to the support layer of the debridement pad (i.e. the surface of the debridement pad that is not in contact with the wound or the back of the debridement pad or the non-wound-contacting surface 312) as shown in FIGS. 3A-3D, or the handle 306 may be detachable as shown in FIG. 3E.

As shown in FIG. 3A, the support layer of the debridement pad 300 can comprise a soft fabric grip 302 attached to the pad for holding the device 300. The debridement pad can also comprise a soft fabric pocket 308 for sliding fingers inside, thus allowing the user to hold the pad (FIG. 3B). Further types of handles attached to the support layer comprise fins 304 that are flat when not in use (FIG. 3C). The fins 304 can comprise a soft or thin back support. The debridement pad may also possess a handle or flap 310 in the form of a smaller central support grip that can be folded up for use (FIG. 3D).

Detachable or external handles 306 may be attached to the outer surface of the support layer by a fastening member 314 (FIG. 3E). The fastening member 314 may be Velcro® or similar hook-and-loop securing member present on both the outer surface of the debridement pad 300 and on the attachment edge of the handle 306, thus allowing the external handle 306 to be removably attached to the pad 300. The detachable or external handle 306 may be a plastic handle.

Alternatively, the outer surface of the support layer 312 of the debridement pad 300 may comprise a thin, flexible layer of silicone, for example, that provides a textured anti-slip surface 316 (FIG. 3F).

EXAMPLE 4

Debridement Device Combined with Infection Detection

This example describes the combination of a debridement device with the ability to detect infection in a wound.

As shown in FIG. 4, one or more diagnostic units or diagnostic disks 402 capable of detecting infection may be combined with a debridement device 400, for example. One or more diagnostic disks 402 may be attached to the handle of the debridement device 400. Such diagnostic disks 402 can be manufactured in sheets 406, comprising reagents printed or deposited on a solid phase, such as filter paper, wherein individual diagnostic disks 402 can be applied, attached to, or embedded in a debridement device 400 using an adhesive or a sticker. Thus, one or more diagnostic disks 402 may be attached to the handle or another part of a debridement device 400 to allow detection of a microbial infection in situ.

The debridement device can be used with or without an infection detection device, as needed. In some embodiments, one or more diagnostic disks 402 are embedded in a debridement device 400, wherein an outermost layer of the debridement device 400 comprises a transparent cover or film to allow visualization of a signal from the diagnostic disks 402. This allows detection of an infection during debridement of a wound or in situ within a single device. In other embodiments, the debridement device 400 may be in fluid communication with an electronic sensor 408 external to the debridement device 400 or partially in contact with the debridement device 400 through, for example, a sensor wire or a probe.

In various embodiments, a diagnostic unit 402 comprises a wicking guide mechanism 404 that allows fluid communication between the wound contacting layer and the reagents of the diagnostic unit or disk 402. The wicking guide mechanism 404 allows wound exudate or materials to be drawn into the diagnostic unit 402, thereby allowing detection of infection. The wicking guide mechanism 404 may comprise threads of fiber. As shown in FIG. 4, the fibres may be gelling fiber. Additional materials that can be used for wicking include non-woven material, fabric, filter paper, or any combination of materials.

EXAMPLE 5

Wicking Guide Mechanism

This example describes wicking guide mechanisms 500 for use with a diagnostic unit 402 for infection detection.

FIGS. 5A-5D illustrate various wicking guide mechanisms 500 that can be used with a sensor or diagnostic unit 402 for detection of infection in combination with a debridement device. Any suitable wicking material 504 can be used. Suitable wicking materials 504 include gelling fiber hydrophilic fibres, non-woven material, fabric, filter paper, or any combination of materials.

As shown in FIG. 5A, the diagnostic or sensor unit can comprise a hole 502 in the bottom of the diagnostic unit, with the interior of the diagnostic unit comprising a wicking material 504 such as gelling fiber, a non-woven material, fabric, filter paper, or any combination of materials. The hole 502 in the bottom allows fluid to flow from the wound contacting layer into the diagnostic unit or disk and to come in contact with the reagents 512 in a reaction layer 514, with the fluid being drawn up by the wicking material 504.

FIG. 5B illustrates the use of threads or fibres as a wicking material 504. The threads or fibres protrude from a hole 502 in the bottom of the sensor unit and allow fluid to flow from the wound contacting layer into the diagnostic or senor unit, with the fluid being drawn up by the wicking material 504. The wicking material 504 may be gelling fiber or any other suitable wicking material 504.

FIG. 5C shows a diagnostic or sensor unit with a dimple feature 506 that allows for wicking to take place. The diagnostic unit may be concave at the top surface, with the dimple feature 506 comprising a suitable wicking material 504 projecting out from the diagnostic unit.

FIG. 5D illustrates use of a hydrophilic or gelling fiber disk 510 as a wicking guide. The hydrophilic or gelling fiber disk 510 is attached to the bottom of the diagnostic unit and allows fluid to be drawn through a hole 502 in the bottom of the sensor unit at the site of attachment or contact with the debridement device. The disk 510 may comprise gelling fibres or any other suitable wicking materia1504, including a non-woven material, fabric, filter paper, or any combination of materials.

EXAMPLE 6

Detection of Infection

This example illustrates various arrangements of indicators, reagents, and diagnostic units 600, 602.

Figure 6A:
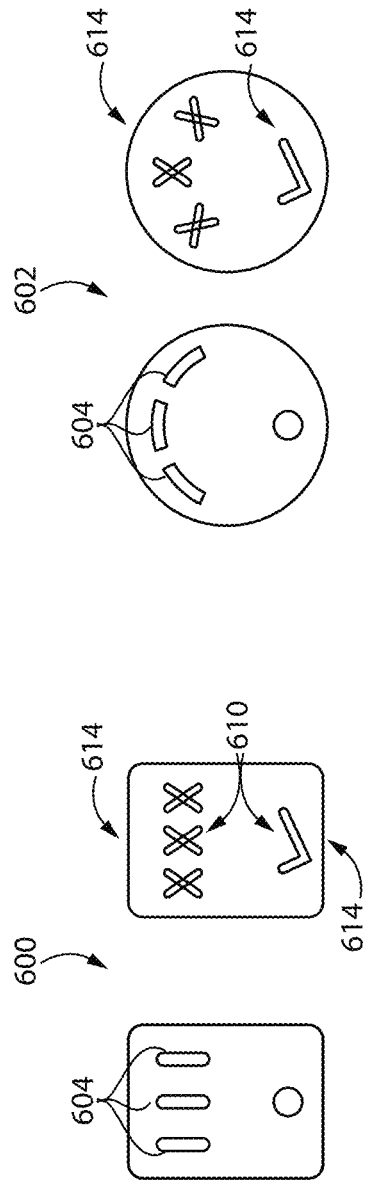
FIGS. 6A-6B illustrate types of diagnostic units 600, 602 for detecting a microbial infection (FIG. 6A), including different shapes (including, but not limited to, square and rectangle and circle shapes), sizes and arrangement of the control and detection panels, as well as different arrangements of reagents 604 and reservoirs or reagent areas 606 (FIG. 6B). The arrangement of the different panels or separators 608 on the diagnostic unit allows for easy differentiation between the control and detection panels. The control(s) and reagents can be arranged in a radial manner with the signal reported in various forms to allow easy and fast detection of a microbial infection.). In some embodiments, one or more reagents of the diagnostic disk interacts with an enzyme marker for a microbial infection to produce a detectable signal in a reporter area 614 of the diagnostic unit 600, 602 which is visible through a window 610, such as a color change or an appearance of a signal or mark.

A diagnostic unit or disk 600, 602 may be a lateral flow or dipstick device. As shown in FIG. 6A, a diagnostic unit comprising reagents 604 for detection of infection of a wound can be in the form of a square, rectangular 600, or round 602. The diagnostic disk 600, 602 may have clear areas or windows 610 for reading a detectable signal that can be of various shapes as shown in FIG. 6A. A detectable signal may include a color change, the appearance of a line or mark, or a digital display, for example. The diagnostic disk 600, 602 may further comprise a control window, indicating that a test has taken place or for comparing with the detectable signal.

Figure 6B:
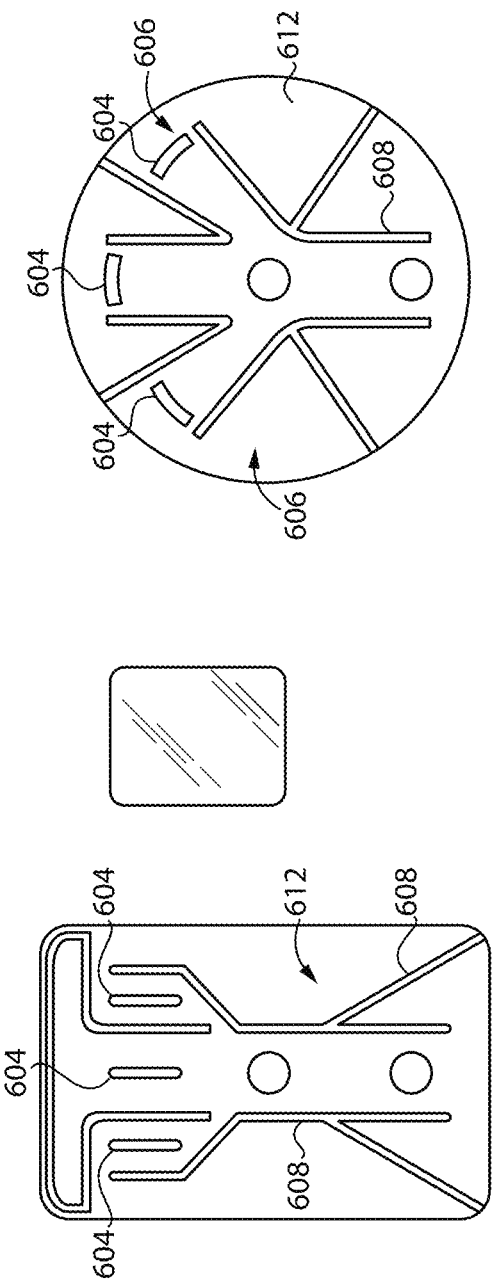
Figure 7:
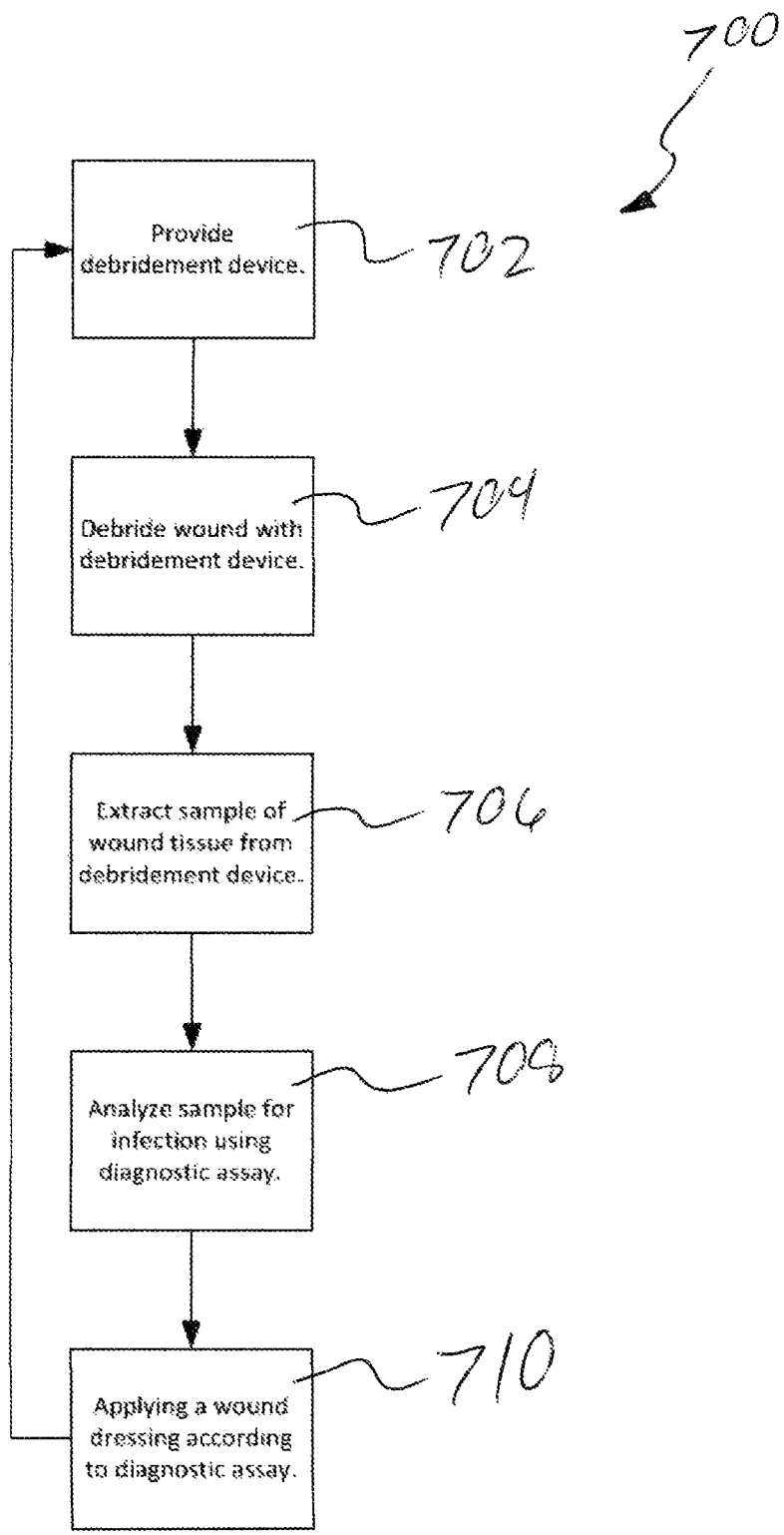
FIG. 7 illustrates a schematic flow chart 700 for one embodiment of this disclosure. More specifically, a debridement device of this disclosure may be provide in box 702. The debridement device may be utilized to debride a wound in box 704. In one aspect of this disclosure, the debridement device may provide a sample of wound tissue in box 706. In box 708, the wound tissue may be analyzed for infection utilizing the methods and devices of this disclosure. In box 710, a wound dressing may be applied to the wound based on the results of the infection analysis of box 708 wherein the wound dressing is specifically tailored to address the type of infection identified in box 708.
Figure 8:
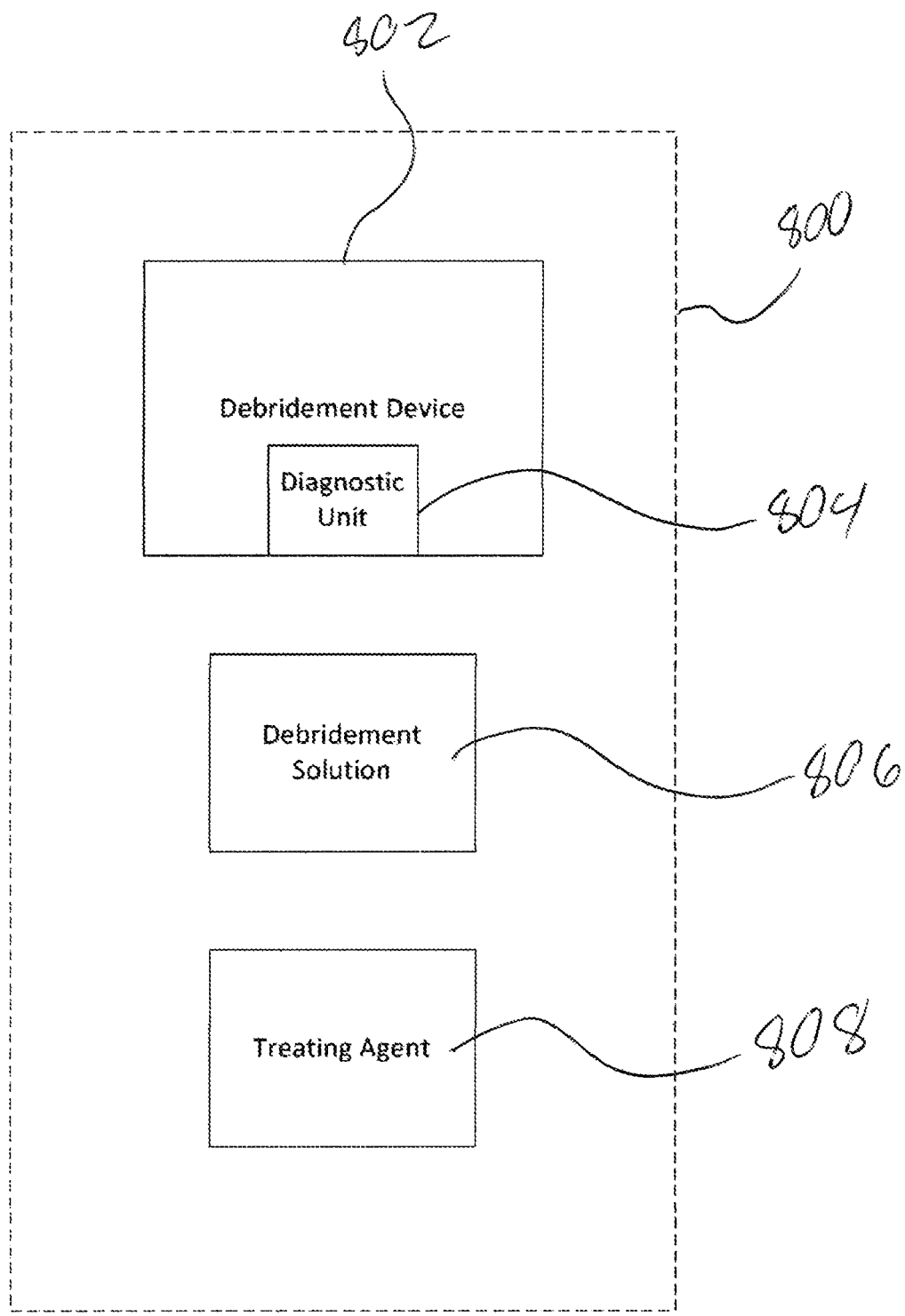
FIG. 8 illustrates one non-exclusive example of a kit 800 of this disclosure. The kit 800 may include a debridement device 802 having a diagnostic unit 804 of this disclosure. The kit 800 may also comprise a debridement solution 806 to assist in the debridement of a wound while using the debridement device 802. Further, the kit 800 may also include a treating agent 808 that assists with treating the wound after debridement. In one non-exclusive example, multiple treating agents 808 may be provided to allow specific treatment of the wound based on the type of infection identified by the diagnostic unit 804.

A diagnostic unit 600, 602 may comprise one or more diagnostic disks comprising reagents 604 or indicators for detection of infection. The diagnostic disk may comprise multiple lanes or sections arranged in a linear or radial configuration (FIG. 6B). Each lane or section comprises reagents or indicators for detection of infection that produce a detectable signal upon change of pH or as a result of an enzymatic reaction, for example. Each reagent 604 or indicator may be printed, sprayed, or deposited onto a solid phase, such as filter paper, with reagent lanes or sections separated by impermeable separators 608. The impermeable separators 608 also demarcate reservoirs 612 comprising wound exudate to be analyzed after wound exudate is drawn into the disk by fluid communication with a wound contacting layer.

Reagents 604 can include reagents or indicators that interact with enzymes or analytes that are associated with the presence of infection. Reagents or indicators may detect the presence of host enzymes or biomarkers that are upregulated in response to infection. Examples of enzymes associated with the presence of infection include, but are not limited to, lysozyme, MPO, cathepsin G, elastase, catalase, lipase, or esterase. Alternatively, reagents or indicators may detect the presence of analytes or enzymes associated with an infectious organism.

Reagents or indicators may also comprise pH-sensitive moieties or pH indicators that signal a change of pH over a variety of pH ranges. In some embodiments, the pH-sensitive moiety presents a visible color change at alkaline pH. In some embodiments, the pH-sensitive moiety presents a visible color change at pH=7.2-9.5. In some embodiments, the pH-sensitive moiety presents a visible color change at pH=7.2-9.0. In some embodiments, the pH-sensitive moiety presents a visible color change at pH=7.2-8.5. In some embodiments, the pH-sensitive moiety presents a visible color change at pH=7.2-8.0. In some embodiments, the pH-sensitive moiety presents a visible color change at pH=7.5-8.5. In some embodiments, the pH-sensitive moiety presents a visible color change at pH=7.5-9.0. In some embodiments, the pH-sensitive moiety presents a visible color change at pH=8.0-9.0. In some embodiments, the pH-sensitive moiety presents a visible color change at pH=7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, or 9.5, or increments thereof.

In some embodiments, the pH-sensitive moiety presents a visible color change at neutral pH. In some embodiments, the pH-sensitive moiety presents a visible color change at pH=6.9, 7.0, or 7.1, or increments thereof.

In some embodiments, the pH-sensitive moiety presents a visible color change at acidic pH. In some embodiments, the pH-sensitive moiety presents a visible color change at pH=4.5-6.8. In some embodiments, the pH-sensitive moiety presents a visible color change at pH=4.5-6.5. In some embodiments, the pH-sensitive moiety presents a visible color change at pH=5.0-6.8. In some embodiments, the pH-sensitive moiety presents a visible color change at pH=5.4-6.8. In some embodiments, the pH-sensitive moiety presents a visible color change at pH=5.4-6.5. In some embodiments, the pH-sensitive moiety presents a visible color change at pH=4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9, or increments thereof.

In some embodiments, the pH-sensitive moiety is bromothymol blue, phenol red, bromophenol red, chlorophenol red, thymol blue, bromocresol green, bromocresol purple, nitrazine yellow, or other sulfonephthalein dyes.

In some embodiments, the diagnostic disk 600, 602 comprises a solid phase material selected from the group consisting of paper, viscose, regenerated cellulose, glass fiber, and similar material.

EXAMPLE 7

Anti-Biofilm Fabric Material

This example describes fabric material for breaking down biofilm and absorbing disrupted biofilm, associated microorganisms, and other wound debris.

The fabric material may comprise gel-forming fibres and an anti-biofilm agent. The gel-forming fibres may comprise carboxymethylcellulose. In some instances, the gel-forming fibres comprise cellulose, carboxymethylcellulose (CMC), carboxyethylcellulose, AQUACEL®, oxidized cellulose (or a derivative thereof), cellulose ethyl sulfonate, other chemically modified cellulose, pectin, alginate, chitosan, modified chitosan, hyaluronic acid, polysaccharide, or gum-derived polymer, or any combination thereof.

The fabric material may further comprise an anti-biofilm agent. The anti-biofilm agent may be ethylenediaminetetraacetic acid (EDTA), tetrasodium EDTA, disodium EDTA, epigallocatechin gallate (EGCG), ellagic acid, esculetin, fisetin, reserpine, quercetin, linoleic acid, berberine, chitosan, eugenol, curcumin, synthetic halogenated furanone (F-56), Peptide 1018, CFT073 group-II capsular polysaccharide (Serotype K2), Pel polysaccharide, Psl polysaccharide, sophorolipid, colistin, nisin, subtilin, epidermin, gallidermin, sodium citrate, tannic acid, deoxyribonuclease I, glycoside hydrolase, bacteriophage-encoded endolysin (PlyC), silver, octenidine hydrochloride, chlorhexidine, cadexomer iodine, polyhexamethylene biguanide, usnic acid, benzethonium chloride (BC), aryl rhodanines, cis-2-decenoid acid (C2DA), or dispersin B.

The fabric material comprising gel-forming fibres and an anti-biofilm agent may be used on a wound. Application of the fabric material on the wound can result in disruption of the biofilm and/or adsorption of the disrupted biofilm. The fabric material may also sequester wound fluid, bacteria, metal ions, and/or other wound debris. The fabric material may improve susceptibility of microorganisms to antimicrobial agents and/or reduce microbial burden.

EXAMPLE 8

Foam Debridement Device

This example describes devices for debridement comprising one or more foams.

One or more foams may be attached to the handle of the debridement device. The one or more foams may be the debridement device. The one or more foams may comprise open pore foams. The one or more foams may comprise a first side comprising a rough texture and a second side comprising a smooth texture. The one or more foams may comprise a rough texture and a smooth texture on the same side. The one or more foams may comprise various materials such as polyurethane, polyethylene, a silicone resin, a natural and synthetic rubber, polyglycolic acid, polylactic acid, or a copolymer thereof; a synthetic polymer, such as polyvinyl alcohol and polyvinylpyrolidone; a natural polymer, such as collagen, gelatin, karaya gum, guar gum, hyaluronic acid, sodium alginate, chitin, chitosan, fibrin, and cellulose, or a synthetic polymer derived therefrom; and a mixture thereof. The one or more foams may comprise polyurethane. The one or more foams may comprise a height in a range of about 1 centimeter to about 5 centimeters. The one or more foams may comprise a width in a range of about 1 centimeter to about 10 centimeters. The one or more foams may comprise a length in a range of about 1 centimeter to about 15 centimeter.

In use, the foam comprising a first side comprising a rough texture may be used to gently scrub the wound area. The foam may be in a butterfly shape such that the first side is hidden. Following scrubbing of the wound area, the foam comprising a second side comprising a smooth texture may be used to absorb the wound debris and wound liquid.

The debridement devices comprising one or more foams may be combined with the ability to detect infection in a wound. One or more diagnostic units or diagnostic disks capable of detecting infection may be combined with the debridement devices comprising one or more foams.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A debridement device having a wound contacting layer for debridement of a wound, the debridement device comprising:
 a stick comprising an end portion defining a base layer, wherein the base layer is flat;
 a layer of gel-forming fibres surrounding the base layer; and
 a layer of bristles in direct contact with the gel-forming fibres, wherein the layer of bristles surrounds the layer of gel-forming fibres;
 wherein the layer of bristles is configured to directly contact the wound and is directly adjacent the layer of gel-forming fibres; and
 wherein the layer of gel-forming fibres is partially positioned on opposite sides of the flat base layer.

2. The device of claim 1, wherein the layer of bristles comprises a pile of monofilaments or fibres.

3. The device of claim 2, wherein the layer of bristles comprises nylon, acetal, polypropylene, acrylic, polyvinyl chloride (PVC), polycarbonate, silicone, wool, or any combination thereof.

4. The device of claim 1, wherein the layer of bristles comprises filaments arranged perpendicular to the wound contacting layer.

5. The device of claim 1, wherein the layer of gel-forming fibres are woven or knitted.

6. The device of claim 1, wherein the layer of gel-forming fibres have an absorbency between 10 g/g and 50 g/g, and resists lateral spread of a fluid upon absorption.

7. The device of claim 1, further comprising anti-biofilm agents, metal chelators, surfactants, or any combination thereof.

8. The device of claim 1, further comprising one or more support layers in contact with the layer of gel-forming fibres, wherein the support layer comprises foam, fabric, blended fabric, paper, polymer, plastic, or any combination thereof.

9. The device of claim 1, further comprising a diagnostic unit in fluid communication with the layer of gel-forming fibres, wherein the diagnostic unit comprises at least one of an enzyme-based assay or an electronic sensor.

10. The device of claim 9, wherein the diagnostic unit comprises one or more diagnostic disks, comprising:
 a) a reaction layer comprising one or more reagents configured to interact with a target enzyme indicative of a microbial infection, wherein the reagents are affixed to a solid phase;
 b) each reagent is sprayed, printed, or deposited in a reagent area separated by impermeable separators;
 c) each reagent area comprises a reporter area wherein a color, color change, or other detectable signal is observed; and
 d) a transparent cover comprising a window for visualizing the signal in the reporter area.

11. The device of claim 9, wherein the fluid communication comprises one or more of a wicking material that comprises hydrophilic fibres, gelling fibres, or filter paper.

12. The device of claim 1, wherein the layer of gel-forming fibres is configured to absorb material dislodged by the bristles during debridement of the wound.

13. The device of claim 12, wherein the material is operable to pass through the bristles directly from the wound to the layer of gel-forming fibres.

14. The device of claim 1, wherein the layer of gel-forming fibres circumferentially surrounds the base layer.

15. A method of detecting a wound infection, comprising:
 providing the debridement device of claim 1;
 debriding a wound using the debridement device;
 extracting a sample of wound tissue from the debridement device; and
 analyzing the sample for presence of a microbial infection using a diagnostic assay.

16. The method of claim 15, wherein the extracting and analyzing step comprises utilizing one or more diagnostic disk that utilizes a wicking material to be in fluid communication with the debridement device, the diagnostic disks comprising a reaction layer with one or more reagents that are configured to interact with a target enzyme indicative of a microbial infection, wherein each reagent is aligned with a reporter area wherein a color, color change, or other detectable signal is observable as part of the analyzing step.

17. The method of claim 15, further comprising applying a wound dressing with an antimicrobial agent according to the diagnostic assay.

18. A kit for debridement of a wound, comprising:
 the debridement device of claim 1;
 a solution for assisting in debridement of the wound comprising one or more of antimicrobial agents, antibiofilm agents, metal chelators, or surfactants; and
 a treating agent comprising at least one of an antimicrobial or an anti-biofilm composition.

19. The kit of claim 18, further comprising: a diagnostic unit in fluid communication with the debridement device, wherein the diagnostic unit comprises at least one of an enzyme-based assay, an electronic sensor, or one or more reagents for indicating infection of the wound.

20. The kit of claim 18, further wherein the wound contacting layer comprises one or more foams.

21. A debridement device, comprising:
a stick comprising an end portion having an outer perimeter; and
a wound-contacting layer for debridement of a wound, the wound-contacting layer consisting essentially of:
  a plurality of bristles operable to directly contact the wound; and
  a layer of gel-forming fibres in direct contact with the plurality of bristles;
wherein the layer of gel-forming fibres completely circumferentially surrounds the outer perimeter of the end portion.

22. A debridement device comprising the wound-contacting layer of claim 21, the debridement device further comprising a support layer positioned behind the layer of gel-forming fibres.

* * * * *